(12) United States Patent
Beckedahl et al.

(10) Patent No.: US 8,940,943 B2
(45) Date of Patent: Jan. 27, 2015

(54) COSMETIC PREPARATIONS

(75) Inventors: Burkhard Beckedahl, Düsseldorf (DE); Markus Dierker, Düsseldorf (DE); Rolf Kawa, Monheim (DE); Stefan Brüning, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/813,719

(22) PCT Filed: Jul. 22, 2011

(86) PCT No.: PCT/EP2011/003670
§ 371 (c)(1),
(2), (4) Date: Feb. 1, 2013

(87) PCT Pub. No.: WO2012/016642
PCT Pub. Date: Feb. 9, 2012

(65) Prior Publication Data
US 2013/0131188 A1 May 23, 2013

(30) Foreign Application Priority Data
Aug. 5, 2010 (EP) .................................... 10172065

(51) Int. Cl.
| C07C 41/00 | (2006.01) |
| C07C 43/00 | (2006.01) |
| A01N 31/14 | (2006.01) |
| A61K 31/08 | (2006.01) |
| A61K 8/33 | (2006.01) |
| A61Q 1/02 | (2006.01) |
| A61Q 1/06 | (2006.01) |
| A61Q 5/12 | (2006.01) |
| A61Q 17/04 | (2006.01) |
| A61Q 19/00 | (2006.01) |
| C07C 43/04 | (2006.01) |
| A61K 47/08 | (2006.01) |
| A61Q 1/00 | (2006.01) |
| A61Q 5/00 | (2006.01) |
| A61Q 15/00 | (2006.01) |

(52) U.S. Cl.
CPC ... *A61K 8/33* (2013.01); *A61Q 1/02* (2013.01); *A61Q 1/06* (2013.01); *A61Q 5/12* (2013.01); *A61Q 17/04* (2013.01); *A61Q 19/00* (2013.01); *C07C 43/04* (2013.01); *A61K 47/08* (2013.01); *A61Q 1/00* (2013.01); *A61Q 5/00* (2013.01); *A61Q 15/00* (2013.01)
USPC ............................ 568/581; 568/671; 514/722

(58) Field of Classification Search
USPC .................. 568/581, 671; 514/722
See application file for complete search history.

(56) References Cited

U.S. PATENT DOCUMENTS

| 4,051,153 | A | | 9/1977 | Cohen et al. | |
| 4,507,279 | A | * | 3/1985 | Okuyama et al. | 424/63 |
| 4,515,711 | A | * | 5/1985 | Chalk et al. | 512/25 |
| 5,705,169 | A | | 1/1998 | Stein et al. | |
| 5,730,960 | A | | 3/1998 | Stein et al. | |
| 5,840,943 | A | | 11/1998 | Ansmann et al. | |
| 6,193,960 | B1 | | 2/2001 | Metzger et al. | |
| 2006/0269496 | A1 | * | 11/2006 | Hwang | 424/70.1 |
| 2007/0281873 | A1 | * | 12/2007 | Okada | 508/579 |
| 2009/0182046 | A1 | * | 7/2009 | Dierker et al. | 514/547 |

FOREIGN PATENT DOCUMENTS

| DE | 19712033 | 9/1998 |
| EP | 0693471 | 1/1996 |
| EP | 0694521 | 1/1996 |
| EP | 0815837 | 1/1998 |
| EP | 0818450 | 1/1998 |
| EP | 1852102 | 11/2007 |
| FR | 2908983 | 11/2006 |
| WO | WO-95/34528 | 12/1995 |

OTHER PUBLICATIONS

Olah, G.A., et al. Catalysis Letters vol. 46, pp. 1-4. Published 1997.*
Gasparrini, F. et al. Tetrahedron vol. 38. pp. 3609-3613. Published 1982.*
Geiseler, G. et al. Physikalische Chemie vol. 65, pp. 750-762. Published 1961.*
"Commission Directive 2005/9/EC", *Official Journal of the European Union* 2005 , 2 pgs.
"PCT International Search Report in PCT/EP2011/003670", Oct. 28, 2010 , 3 pgs.
"Abstract Translation of JP-48005941 B4", Jan. 25, 1973, 2 pgs.
Fiedler, Herbert P. , "Lexikon der Hilfsstoffe", 4th Ed. 1996.
Finkel, P. , "Formulierung josmetischer Sonnenschutzmittel", *SOFW-Journal*, 122 1996 , 543-548.
Finkel, P. , "Formulierung kosmetischer Sonnenschutzmittel", *Parfumerie und Kosmetik*, 80 Mar. 1999 , 7 pgs.
Griffin, William C. , "Calculation of HLB Values of Non-Ionic Surfactants", *Journal of the Scoiety of Cosmetic Chemists* 1954 , 249-256.
Griffin, William C. , "Classification of Surface-Active Agents by "HLB"", *Journal of the Society of Cosmetic Chemists* 1949 , 311-326.
Kirk-Othmer, "Encyclopedia of Chemical Technology", 3rd Ed., vol. 8 1979 , 5 pgs.
Nagai, Kimiko, "The Formation of Esthers from Nerol and I-Linalool in the Presence of Boron Trifluoride Etherate", *Bulletin of the Chemical Society of Japan*, vol. 48(8) 1975 , 6 pgs.

* cited by examiner

*Primary Examiner* — Paul Zarek
*Assistant Examiner* — George W Kosturko
(74) *Attorney, Agent, or Firm* — Servilla Whitney LLC

(57) ABSTRACT

The invention relates to compounds of the general formula (I), where $R_1$ is a branched alkyl(ene) radical having from 10 to 22 carbon atoms and having at least one branch in position 1, 2, 3 or 4 relative to the oxygen atom, $R_2$ is a linear or branched alkyl(ene) radical having from 1 to 13 carbon atoms and $R_1$ and $R_2$ are selected so that the total number of carbon atoms in formula (I) is from 11 to 23. The compounds of the invention are suitable for preparation of or in cosmetic and/or pharmaceutical preparations, in particular as oily substances.

$$R_1-O-R_2 \quad (I)$$

8 Claims, No Drawings

COSMETIC PREPARATIONS

CROSS-REFERENCE TO RELATED APPLICATIONS

This application is the national stage entry of PCT/EP2011/003670, filed on Jul. 22, 2011, which claims priority to European Patent application number EP10172065.4, filed on Aug. 5, 2010, both of which are incorporated herein by reference in their entireties.

FIELD

The invention relates to special dialkyl(ene) ethers and use thereof in cosmetic and/or pharmaceutical preparations and a method of production thereof.

BACKGROUND

The consumer requires preparations for care of the skin and hair to meet a large number of requirements: apart from the cleaning and caring effects, which determine the intended application, value is placed on such diverse parameters as maximum possible dermatological compatibility, good refatting properties, elegant appearance, optimal sensory impression and storage stability.

Preparations that are used for cleaning and care of human skin and the hair as a rule contain, in addition to a number of surface active substances, mainly oily substances and water. The oily substances/emollients used are for example hydrocarbons, ester oils and vegetable and animal oils/fats/waxes. In order to fulfill the high requirements of the market with respect to sensory properties and optimal dermatological compatibility, new oily substances and emulsifier mixtures are constantly being developed and tested. Dialkyl ethers are described as cosmetic oily substances in the prior art, for example in EP 0 815 837 A1. A commercially available dialkyl ether is di-n-octyl ether, which is sold under the trade name Cetiol® OE. In FR 2 908 983 A1, dialkyl ethers are mentioned as suitable ingredients for cosmetic preparations. JP 48 005941 B4 discloses concretely branched dialkyl ethers, which comprise 2-ethylhexanol or 2-butyloctanol residues, as skin-compatible cosmetic ingredients. It is known from EP 1 852 102 A2 that di-n-alkyl ethers, but also di-n-alkyl carbonates, can be used as oil components in cosmetic preparations.

A drawback of the dialkyl(ene) ethers of the prior art is their limited skin compatibility. A further problem to be solved by the present invention was to provide compounds that are improved with respect to sensory perceptions, relative to the compounds of the prior art. In particular, lightness, a "non-greasy" feeling on the skin, softness, spreading capacity, absorption, distributability and oiliness were of interest. Moreover, it should be possible to incorporate the compounds in a large number of cosmetic formulations. Compatibility with crystalline UV filters, pigments and antiperspirant salts was of particular interest. Another problem was to provide compounds that are suitable as substitutes for silicone oils.

SUMMARY

Aspects of the invention relate to a compound of general formula (I) $R_1$—O—$R_2$, wherein $R_1$ represents a branched alkyl(ene) residue with 10 to 22 carbon atoms, wherein at least one branching is located at position 1, 2, 3 or 4 to the oxygen atom; $R_2$ represents a linear or branched alkyl(ene) residue with 1 to 13 carbon atoms; and $R_1$ and $R_2$ are selected so that the total number of carbon atoms in formula (I) is 11 to 23. Also provided are methods of producing a cosmetic and/or pharmaceutical preparation, the method comprising incorporating one or more said compounds in a cosmetic and/or pharmaceutical preparation. Accordingly, another aspect of the invention relates to a cosmetic and/or pharmaceutical preparation comprising 0.1 to 95 wt % of one or more of said compounds in a cosmetically and/or pharmaceutically suitable vehicle.

DETAILED DESCRIPTION

Aspects of the invention relate to compounds of formula (I)

$R_1$—O—$R_2$, wherein $R_1$ represents a branched alkyl(ene) residue with 10 to 22 carbon atoms, wherein at least one branching is located at position 1, 2, 3 or 4 to the oxygen atom $R_2$ represents a linear or branched alkyl(ene) residue with 1 to 13 carbon atoms and $R_1$ and $R_2$ are selected so that the total number of carbon atoms in formula (I) is 11 to 23.

Unless stated otherwise, the alkyl(ene) residues always refer to linear alkyl(ene) residues, i.e. octyl residue=n-octyl, tetradecyl=n-tetradecyl.

Residue $R_1$

The residue $R_1$ represents a branched alkyl(ene) residue with 10 to 22 carbon atoms, wherein at least one branching is located at position 1, 2, 3 or 4 to the oxygen atom.

The positions of the branchings are always designated starting from the oxygen atom of the ether to which the alkyl(ene) residue is bound.

The term alkyl(ene) residue comprises saturated (=alkyl residues) and singly or multiply unsaturated residues (both designated as alkylene residues). A preferred embodiment of the invention relates to compounds of formula (I) in which $R_1$ represents a saturated residue.

The residue $R_1$ is branched, i.e. at least one carbon atom of the alkyl(ene) residue is joined to at least 3 carbon atoms. Residues $R_1$ that have more than one branching and residues that have 2 branchings on one carbon atom and residues $R_1$ that have branched branchings are also included. The further branching(s) can be located both at positions 1, 2, 3 or 4 to the oxygen atom and at the other positions of the alkyl(ene) residue.

Suitable residues $R_1$ are for example branched alkyl(ene) residues with 10 carbon atoms.

One embodiment of the invention relates to compounds of formula (I) in which $R_1$ represents a branched alkyl(ene) residue with 10 carbon atoms, wherein at least one branching is located at position 1, 2, 3 or 4 to the oxygen atom.

Branched alkyl residues with 10 carbon atoms selected from the group consisting of 2-propylheptyl-, 3-methyl-2-propyl-hexyl, 4-methyl-2-propyl-hexyl and 5-methyl-2-propyl-hexyl-, trimethylheptyl-, 3,5-dimethyloctyl-, 2,2-dimethyloctyl-, 1-ethyl-octyl-, 2-ethyl-octyl, 3-ethyl-octyl-, 4-ethyl-octyl-, 1-propyl-heptyl-, 3-propyl-heptyl-, 4-propyl-heptyl- are especially preferred as $R_1$.

Suitable residues $R_1$ are for example branched alkyl(ene) residues with 11 carbon atoms.

One embodiment of the invention relates to compounds of formula (I) in which $R_1$ represents a branched alkyl(ene) residue with 11 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-decyl-, 2-methyl-decyl-, 3-methyl-decyl-, 4-methyl-decyl-, 1-ethyl-nonyl-, 2-ethyl-nonyl-, 3-ethyl-nonyl-, 4-ethyl-nonyl-, 1-propyl-octyl-, 2-propyl-octyl-, 3-propyl-octyl-, 4-propyl-octyl-.

Suitable residues $R_1$ are for example branched alkyl(ene) residues with 12 carbon atoms.

One embodiment of the invention relates to compounds of formula (I) in which $R_1$ represents a branched alkyl(ene) residue with 12 carbon atoms, wherein at least one branching is located at position 1, 2, 3 or 4 to the oxygen atom.

One embodiment of the invention relates to compounds of formula (I) in which $R_1$ represents a residue selected from the group consisting of 1-ethyl-decyl-, 2-ethyl-decyl-, 3-ethyl-decyl-, 4-ethyl-decyl-, 1-butyl-octyl-, 2-butyl-octyl-, 3-butyl-octyl-, 4-butyl-octyl-, 2-hexyl-hexyl-, 2,5,8-trimethyl-nonyl; 2,2,4,6,6-pentamethylheptyl.

Suitable residues $R_1$ are for example branched alkyl(ene) residues with 13 carbon atoms.

One embodiment of the invention relates to compounds of formula (I) in which $R_1$ represents a branched alkyl(ene) residue with 13 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-dodecyl-, 2-methyl-dodecyl-, 3-methyl-dodecyl-, 4-methyl-dodecyl-, 1-ethyl-undecyl-, 2-ethyl-undecyl-, 3-ethyl-undecyl-, 4-ethyl-undecyl-, 1-propyl-decyl-, 2-propyl-decyl-, 3-propyl-decyl-, 4-propyl-decyl-, tetramethyl-nonyl.

Suitable residues $R_1$ are for example branched alkyl(ene) residues with 14 carbon atoms.

One embodiment of the invention relates to compounds of formula (I) in which $R_1$ represents a branched alkyl(ene) residue with 14 carbon atoms, wherein at least one branching is located at position 1, 2, 3 or 4 to the oxygen atom.

One embodiment of the invention relates to compounds of formula (I) in which $R_1$ represents a residue selected from the group consisting of 1-ethyl-dodecyl-, 2-ethyl-dodecyl-, 3-ethyl-dodecyl-, 4-ethyl-dodecyl-, 1-butyl-decyl-, 2-butyl-decyl-, 3-butyl-decyl-, 4-butyl-decyl-, 1-hexyl-octyl-, 2-hexyl-octyl-, 3-hexyl-octyl-, 4-hexyl-octyl-.

Suitable residues $R_1$ are for example branched alkyl(ene) residues with 15 carbon atoms.

One embodiment of the invention relates to compounds of formula (I) in which $R_1$ represents a branched alkyl(ene) residue with 15 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-tetradecyl-, 2-methyl-tetradecyl-, 3-methyl-tetradecyl-, 4-methyl-tetradecyl-, 1-ethyl-tridecyl-, 2-ethyl-tridecyl-, 3-ethyl-tridecyl-, 4-ethyl-tridecyl-, 1-propyl-dodecyl-, 2-propyl-dodecyl-, 3-propyl-dodecyl-, 4-propyl-dodecyl-, 3,7,11-trimethyl-dodecyl-.

Suitable residues $R_1$ are for example branched alkyl(ene) residues with 16 carbon atoms.

One embodiment of the invention relates to compounds of formula (I) in which $R_1$ represents a branched alkyl(ene) residue with 16 carbon atoms, wherein at least one branching is located at position 1, 2, 3 or 4 to the oxygen atom.

One embodiment of the invention relates to compounds of formula (I) in which $R_1$ represents a residue selected from the group consisting of 1-ethyl-tetradecyl-, 2-ethyl-tetradecyl-, 3-ethyl-tetradecyl-, 4-ethyl-tetradecyl-, 1-butyl-dodecyl-, 2-butyl-dodecyl-, 3-butyl-dodecyl-, 4-butyl-dodecyl-, 1-hexyl-decyl-, 2-hexyl-decyl-, 3-hexyl-decyl-, 4-hexyl-decyl-, 2,5,8,11-tetramethyl-undecyl-.

Suitable residues $R_1$ are for example branched alkyl(ene) residues with 17 carbon atoms. One embodiment of the invention relates to compounds of formula (I) in which $R_1$ represents a branched alkyl(ene) residue with 17 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-hexadecyl-, 2-methyl-hexadecyl-, 3-methyl-hexadecyl-, 4-methyl-hexadecyl-, 1-ethyl-pentadecyl-, 2-ethyl-pentadecyl-, 3-ethyl-pentadecyl-, 4-ethyl-pentadecyl-, 1-propyl-tetradecyl-, 2-propyl-tetradecyl-, 3-propyl-tetradecyl-, 4-propyl-tetradecyl-, 1-butyl-tridecyl-, 2-butyl-tridecyl-, 3-butyl-tridecyl-, 4-butyl-tridecyl-, 1-pentyl-dodecyl-, 2-pentyl-dodecyl-, 3-pentyl-dodecyl-, 4-pentyl-dodecyl-.

Suitable residues $R_1$ for example branched alkyl(ene) residues with 18 carbon atoms. One embodiment of the invention relates to compounds of formula (I) in which $R_1$ represents a branched alkyl(ene) residue with 18 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-heptadecyl-, 2-methyl-heptadecyl-, 3-methyl-heptadecyl-, 4-methyl-heptadecyl-, 1-ethyl-hexadecyl-, 2-ethyl-hexadecyl-, 3-ethyl-hexadecyl-, 4-ethyl-hexadecyl-, 1-propyl-pentadecyl-, 2-propyl-pentadecyl-, 3-propyl-pentadecyl-, 4-propyl-pentadecyl-, 1-butyl-tetradecyl-, 2-butyl-tetradecyl-, 3-butyl-tetradecyl-, 4-butyl-tetradecyl-, 1-pentyl-tridecyl-, 2-pentyl-tridecyl-, 3-pentyl-tridecyl-, 4-pentyl-tridecyl-, 1-hexyl-dodecyl-, 2-hexyl-dodecyl-, 3-hexyl-dodecyl-, 4-hexyl-dodecyl-.

Suitable residues $R_1$ are for example branched alkyl(ene) residues with 19 carbon atoms.

One embodiment of the invention relates to compounds of formula (I) in which $R_1$ represents a branched alkyl(ene) residue with 19 carbon atoms, wherein at least one branching is located at position 1, 2, 3 or 4 to the oxygen atom.

One embodiment of the invention relates to compounds of formula (I) in which $R_1$ represents a residue selected from the group consisting of
1-methyl-octadecyl-, 2-methyl-octadecyl-, 3-methyl-octadecyl-, 4-methyl-octadecyl-, 1-ethyl-heptadecyl-, 2-ethyl-heptadecyl-, 3-ethyl-heptadecyl-, 4-ethyl-heptadecyl-, 1-propyl-hexadecyl-, 2-propyl-hexadecyl-, 3-propyl-hexadecyl-, 4-propyl-hexadecyl-, 1-butyl-pentadecyl-, 2-butyl-pentadecyl-, 3-butyl-pentadecyl-, 4-butyl-pentadecyl-, 1-pentyl-tetradecyl-, 2-pentyl-tetradecyl-, 3-pentyl-tetradecyl-, 4-pentyl-tetradecyl-, 1-hexyl-tridecyl-, 2-hexyl-tridecyl-, 3-hexyl-tridecyl-, 4-hexyl-tridecyl-, 1-heptyl-dodecyl-, 2-heptyl-dodecyl-, 3-heptyl-dodecyl-, 4-heptyl-dodecyl-, 1-octyl-undecyl-, 2-octyl-undecyl-, 3-octyl-undecyl-, 4-octyl-undecyl-, 1-nonyl-dodecyl-, 2-nonyl-dodecyl-, 3-nonyl-dodecyl-, 4-nonyl-dodecyl-, 1-hexyl-tridecyl-, 2-hexyl-tridecyl-, 3-hexyl-tridecyl-, 4-hexyl-tridecyl-.

Suitable residues $R_1$ are for example branched alkyl(ene) residues with 20 carbon atoms. One embodiment of the invention relates to compounds of formula (I) in which $R_1$ represents a branched alkyl(ene) residue with 20 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-nonadecyl-, 2-methyl-nonadecyl-, 3-methyl-nonadecyl-, 4-methyl-nonadecyl-, 1-ethyl-octadecyl-, 2-ethyl-octadecyl-, 3-ethyl-octadecyl-, 4-ethyl-octadecyl-, 1-propyl-heptadecyl-, 2-propyl-heptadecyl-, 3-propyl-heptadecyl-, 4-propyl-heptadecyl-, 1-butyl-hexadecyl-, 2-butyl-hexadecyl-, 3-butyl-hexadecyl-, 4-butyl-hexadecyl-, 1-pentyl-pentadecyl-, 2-pentyl-pentadecyl-, 3-pentyl-pentadecyl-, 4-pentyl-pentadecyl-, 1-hexyl-tetradecyl-, 2-hexyl-tetradecyl-, 3-hexyl-tetradecyl-, 4-hexyl-tetradecyl-, 1-heptyl-tridecyl-, 2-heptyl-tridecyl-, 3-heptyl-tridecyl-, 4-heptyl-tridecyl-, 1-octyl-dodecyl-, 2-octyl-dodecyl-, 3-octyl-dodecyl-, 4-octyl-dodecyl-, 1-nonyl-undecyl-, 2-nonyl-undecyl-, 3-nonyl-undecyl-, 4-nonyl-undecyl-, 1-decyl-decyl-, 2,5,8,11,13-pentamethyl-tridecyl-[=pentaisobutyl], 3,7,11,15-tetramethyl-hexadecyl-.

Suitable residues $R_1$ are for example branched alkyl(ene) residues with 21 carbon atoms. One embodiment of the invention relates to compounds of formula (I) in which $R_1$ represents a branched alkyl(ene) residue with 21 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-eicosyl-, 2-methyl-eicosyl-, 3-methyl-eicosyl-, 4-methyl-eicosyl-, 1-ethyl-nonadecyl-, 2-ethyl-nonadecyl-, 3-ethyl-nonadecyl-, 4-ethyl-nonadecyl-, 1-propyl-octadecyl-, 2-propyl-octadecyl-, 3-propyl-octadecyl-, 4-propyl-octadecyl-, 1-butyl-heptdecyl-, 2-butyl-heptdecyl-, 3-butyl-heptdecyl-, 4-butyl-heptdecyl-, 1-pentyl-hexadecyl-, 2-pentyl-hexadecyl-, 3-pentyl-hexadecyl-, 4-pentyl-hexadecyl-, 1-hexyl-pentadecyl-, 2-hexyl-pentadecyl-, 3-hexyl-pentadecyl-, 4-hexyl-pentadecyl-, 1-heptyl-tetradecyl-, 2-heptyl-tetradecyl-, 3-heptyl-tetradecyl-, 4-heptyl-tetradecyl-, 1-octyl-tridecyl-, 2-octyl-tridecyl-, 3-octyl-tridecyl-, 4-octyl-tridecyl-, 1-nonyl-dodecyl-, 2-nonyl-dodecyl-, 3-nonyl-dodecyl-, 1-decyl-undecyl-, 2-decyl-undecyl-.

Suitable residues $R_1$ are for example branched alkyl(ene) residues with 22 carbon atoms. One embodiment of the invention relates to compounds of formula (I) in which $R_1$ represents a branched alkyl(ene) residue with 21 carbon atoms, wherein at least one branching is located at position 1, 2, 3 or 4 to the oxygen atom.

One embodiment of the invention relates to compounds of formula (I) in which $R_1$ represents a residue selected from the group consisting of 1-methyl-heneicosyl-, 2-methyl-heneicosyl-, 3-methyl-heneicosyl-, 4-methyl-heneicosyl-, 1-ethyl-eicosyl-, 2-ethyl-eicosyl-, 3-ethyl-eicosyl-, 4-ethyl-eicosyl-, 1-propyl-nonadecyl-, 2-propyl-nonadecyl-, 3-propyl-nonadecyl-, 4-propyl-nonadecyl-, 1-butyl-octadecyl-, 2-butyl-octadecyl-, 3-butyl-octadecyl-, 4-butyl-octadecyl-, 1-pentyl-heptadecyl-, 2-pentyl-heptadecyl-, 3-pentyl-heptadecyl-, 4-pentyl-heptadecyl-, 1-hexyl-hexadecyl-, 2-hexyl-hexadecyl-, 3-hexyl-hexadecyl-, 4-hexyl-hexadecyl-, 1-heptyl-pentadecyl-, 2-heptyl-pentadecyl-, 3-heptyl-pentadecyl-, 4-heptyl-pentadecyl-, 1-octyl-tetradecyl-, 2-octyl-tetradecyl-, 3-octyl-tetradecyl-, 4-octyl-tetradecyl-, 1-nonyl-tridecyl-, 2-nonyl-tridecyl-, 3-nonyl-tridecyl-, 4-nonyl-tridecyl-, 1-decyl-dodecyl-, 2-decyl-dodecyl-.

Residue $R_2$

The residue $R_2$ represents a linear or branched alkyl(ene) residue with 1 to 14 carbon atoms.

The term alkyl(ene) residue comprises saturated (=alkyl residues) and singly or multiply unsaturated residues (both designated as alkylene residues). A preferred embodiment of the invention relates to compounds of formula (I) in which $R_2$ represents a saturated residue.

The residue $R_2$ can be a branched alkyl(ene) residue, i.e. at least one carbon atom of the alkyl(ene) residue is joined to at least 3 carbon atoms. Residues $R_2$ that have more than one branching, and residues that have 2 branchings on one carbon atom, and residues $R_2$ that have branched branchings, are also included. The further branching(s) can be located both at positions 1, 2, 3 or 4 to the oxygen atom and at the other positions of the alkyl(ene) residue.

If $R_2$ represents a branched alkyl(ene) residue, it is preferable that this has at least one branching in position 1, 2, 3 or 4 to the oxygen atom. The positions of the branchings are always designated starting from the oxygen atom of the ether to which the alkyl(ene) residue is bound.

Suitable residues $R_2$ are for example methyl-, ethyl-.

Suitable residues $R_2$ are linear alkyl(ene) residues with 3 carbon atoms such as for example propyl-; singly unsaturated residues such as 1-propenyl-, 2-propenyl-, branched residues such as for example methyl- or ethyl-.

Suitable residues $R_2$ are linear alkyl(ene) residues with 4 carbon atoms such as for example butyl-; singly unsaturated residues such as for example but-2-enyl, but-3-enyl, but-1-enyl; branched residues $R_2$ with 4 carbon atoms are designated as i-butyl residues. Examples of i-butyl residues are 1-methyl-propyl-, 2-methyl-propyl-, 1,1-dimethylethyl-.

Suitable residues $R_2$ are linear alkyl(ene) residues with 5 carbon atoms such as for example pentyl-; singly unsaturated residues such as for example 1-pentenyl-, 2-pentenyl-, 3-pentenyl-, 4-pentenyl-. Branched residues $R_2$ with 5 carbon atoms are designated as i-pentyl residues. Examples of i-pentyl residues are 1-methylbutyl-, 2-methylbutyl-, 3-methylbutyl, 1-ethylpropyl-, 1,1-dimethylpropyl, 1,2-dimethylpropyl, 2,2-dimethylpropyl-.

Suitable residues $R_2$ are linear alkyl(ene) residues with 6 carbon atoms, such as for example hexyl-; singly unsaturated residues such as for example 1-hexenyl, 2-hexenyl, 3-hexenyl, 4-hexenyl-, 5-hexenyl-. Branched residues $R_2$ with 6 carbon atoms are designated as i-hexyl residues. Examples of i-hexyl residues are 1-methylpentyl-, 2-methylpentyl, 3-methylpentyl, 4-methylpentyl, 1-ethylbutyl-, 2-ethylbutyl-, 1,2-dimethylbutyl-, 1,3-dimethylbutyl-, 2,2-dimethylbutyl-, 2,3-dimethylbutyl-, 3,3-dimethylbutyl-.

Suitable residues $R_2$ are linear alkyl(ene) residues with 7 carbon atoms, such as for example heptyl-; singly unsaturated residues, such as for example 1-heptenyl, 2-heptenyl, 3-heptenyl-, 4-heptenyl-, 5-heptenyl, 6-heptenyl-. Branched residues $R_2$ with 7 carbon atoms are designated as i-heptyl residues. Examples of i-heptyl residues are methyl-hexyl-(1-methyl-hexyl, 2-methyl-hexyl, 3-methyl-hexyl, 4-methyl-hexyl, 5-methyl-hexyl-), ethyl-pentyl-(1-ethyl-pentyl-, 2-ethyl-pentyl, 3-ethyl-pentyl or 4-ethyl-pentyl-), propyl-butyl-(1-propyl-butyl-, 2-propyl-butyl-, 3-propyl-butyl-), dimethyl-pentyl- (for example 1,1-dimethyl-pentyl-, 1,2-dimethyl-pentyl-, 1,3-dimethyl-pentyl-, 1,4-dimethyl-pentyl-, 2,2-dimethyl-pentyl-, 2,3-dimethyl-pentyl-, 2,4-dimethyl-pentyl-), trimethyl-butyl- (for example 1,1,2-trimethyl-butyl, 1,2,3-trimethylbutyl) or methyl-ethyl-butyl- (for example 1-methyl-2-ethyl-butyl-). 1-Ethyl-pentyl is preferred as i-heptyl residue $R_2$.

Suitable residues $R_2$ are linear alkyl(ene) residues with 8 carbon atoms, such as for example octyl-; singly unsaturated residues, such as for example 1-octenyl-, 2-octenyl-, 3-octenyl-, 4-octenyl-, 5-octenyl-, 6-octenyl-, 7-octenyl-. Branched residues $R_2$ with 8 carbon atoms are designated as i-octyl residues. Examples of i-octyl residues are methyl-heptyl-(1- methyl-heptyl, 2-methyl-heptyl, 3-methyl-heptyl, 4-methyl-heptyl, 5-methyl-heptyl-, 6-methyl-heptyl-), ethyl-hexyl-(1-ethyl-hexyl-, 2-ethyl-hexyl, 3-ethyl-hexyl- or 4-ethyl-hexyl-), propyl-pentyl- (1-propyl-pentyl-, 2-propyl-pentyl-, 3-propyl-pentyl-), butyl-butyl-(for example 1-butyl-butyl, 2-butyl-butyl or 3-butyl-butyl-), dimethyl-hexyl- (for example 1,1-dimethyl-hexyl-, 1,2-dimethyl-hexyl-, 1,3-dimethyl-hexyl-, 1,4-dimethyl-hexyl-, 2,2-dimethyl-hexyl-, 2,3-dimethyl-hexyl-, 2,4-dimethyl-hexyl-), trimethyl-pentyl-(for example 1,1,2-trimethyl-pentyl, 1,2,3-trimethylpentyl, 2,4,4-trimethyl-pentyl) or methyl-ethyl-pentyl-(for example 1-methyl-2-ethyl-pentyl-) or tetramethyl-butyl (for example 1, 1,3,3-tetramethyl-butyl). 2,4,4-Trimethyl-pentyl is preferred as i-octyl residue $R_2$.

Suitable residues $R_2$ are linear alkyl(ene) residues with 9 carbon atoms, such as for example nonyl-; singly unsaturated residues, such as for example 1-nonenyl-, 2-noneyl-, 3-noneyl-, 4-noneyl-, 5-noneyl-, 6-noneyl-, 7-noneyl-, 8-noneyl-. Branched residues $R_2$ with 9 carbon atoms are designated as i-nonyl residues. Examples of i-nonyl residues are methyl-octyl- (1-methyl-octyl-, 2-methyl-octyl, 3-methyl-octyl, 4-methyl-octyl, 5-methyl-octyl-, 6-methyl-octyl-, 7-methyl-octyl-), ethyl-heptyl- (1-ethyl-heptyl-, 2-ethyl-heptyl, 3-ethyl-heptyl, 4-ethyl-heptyl, 5-ethyl-heptyl or 6-ethyl-heptyl-), propyl-hexyl- (1-propyl-hexyl-, 2-propyl-hexyl-, 3-propyl-hexyl-, 4-propyl-hexyl-, 5-propyl-hexyl-), butyl-pentyl- (for example 1-butyl-pentyl, 2-butyl-pentyl or 3-butyl-pentyl-), dimethyl-heptyl- (for example 1,1-dimethyl-heptyl-, 1,2-dimethyl-heptyl-, 1,3-dimethyl-heptyl-, 1,4-dimethyl-heptyl-, 2,2-dimethyl-heptyl-, 2,3-dimethyl-heptyl-, 2,4-dimethyl-heptyl-), trimethyl-hexyl-(for example 1,1,2-trimethyl-hexyl, 1,2,3-trimethyl-hexyl, 2-methyl-4,4-dimethyl-hexyl, 3,5,5-trimethyl-hexyl-) or methyl-ethyl-hexyl- (for example 1-methyl-2-ethyl-hexyl-). Trimethyl-hexyl residues and 3,5-dimethyl-n-heptyl- are preferred as i-nonyl residue $R_2$.

Suitable residues $R_2$ are linear alkyl(ene) residues with 10 carbon atoms, such as for example decyl-, singly unsaturated residues such as for example 1-decenyl-, 2-decenyl-, 3-decenyl-, 4-decenyl and branched alkyl(ene) residues with 10 carbon atoms, such as for example 2-propylheptyl-, 3-methyl-2-propyl-hexyl, 4-methyl-2-propyl-hexyl and 5-methyl-2-propyl-hexyl-, trimethylheptyl-, 3,5-dimethyloctyl-, 2,2-dimethyloctyl-, 1-ethyl-octyl-, 2-ethyl-octyl, 3-ethyl-octyl-, 4-ethyl-octyl-, 1-propyl-heptyl-, 3-propyl-heptyl-, 4-propyl-heptyl-.

Suitable residues $R_2$ are for example linear alkyl(ene) residues with 11 carbon atoms such as for example undecyl-, singly unsaturated residues such as for example 1-undecenyl-, 2-undecenyl-, 3-undecenyl-, 4-undecenyl and branched alkyl(ene) residues with 11 carbon atoms, such as for example 1-methyl-decyl-, 2-methyl-decyl-, 3-methyl-decyl-, 4-methyl-decyl-, 1-ethyl-nonyl-, 2-ethyl-nonyl-, 3-ethyl-nonyl-, 4-ethyl-nonyl-, 1-propyl-octyl-, 2-propyl-octyl-, 3-propyl-octyl-, 4-propyl-octyl-.

Suitable residues $R_2$ are for example linear alkyl(ene) residues with 12 carbon atoms such as for example dodecyl-, singly unsaturated residues such as for example 1-dodecenyl-, 2-dodecenyl-, 3-dodecenyl-, 4-dodecenyl, 5-dodecenyl-, and branched alkyl(ene) residues with 12 carbon atoms, such as for example 1-ethyl-decyl-, 2-ethyl-decyl-, 3-ethyl-decyl-, 4-ethyl-decyl-, 1-butyl-octyl-, 2-butyl-octyl-, 3-butyl-octyl-, 4-butyl-octyl-, 2-hexyl-hexyl-, 2,5,8-trimethyl-nonyl, 2,2,4,6,6-pentamethylheptyl-.

Suitable residues $R_2$ are for example linear alkyl(ene) residues with 13 carbon atoms such as for example tridecyl-, singly unsaturated residues such as for example 1-tridecenyl-, 2-tridecenyl-, 3-tridecenyl-, 4-tridecenyl-, 5-tridecenyl- and branched alkyl(ene) residues with 13 carbon atoms, such as for example 1-methyl-dodecyl-, 2-methyl-dodecyl-, 3-methyl-dodecyl-, 4-methyl-dodecyl-, 1-ethyl-undecyl-, 2-ethyl-undecyl-, 3-ethyl-undecyl-, 4-ethyl-undecyl-, 1-propyl-decyl-, 2-propyl-decyl-, 3-propyl-decyl-, 4-propyl-decyl-, tetramethyl-nonyl-.

Suitable residues $R_2$ are for example linear alkyl(ene) residues with 14 carbon atoms such as for example tetradecyl-; singly unsaturated residues such as for example 1-tetradecenyl-, 2-tetradecenyl-, 3-tetradecenyl-, 4-tetradecenyl-, 5-tetradecenyl-, 6-tetradecenyl-, and branched alkyl(ene) residues with 14 carbon atoms, such as for example 1-ethyl-dodecyl-, 2-ethyl-dodecyl-, 3-ethyl-dodecyl-, 4-ethyl-dodecyl-, 1-butyl-decyl-, 2-butyl-decyl-, 3-butyl-decyl-, 4-butyl-decyl-, 1-hexyl-octyl-, 2-hexyl-octyl-, 3-hexyl-octyl-, 4-hexyl-octyl-.

A characteristic feature of the compounds according to formula (I) is the total number of carbon atoms in the molecule. The compounds have at least 11 and at most 23 carbon atoms in total, wherein those compounds may be preferred that have at least 14 carbon atoms in the molecule and at most 23 carbon atoms. In particular, those compounds of formula (I) are preferred that comprise 14 to 20 carbon atoms.

Isomers

If the residues $R_1$ or $R_2$ have a chiral carbon atom, both the ethers of the racemates and the ethers of the individual enantiomers are comprised.

One embodiment of the invention relates to compounds of formula (I), $R_1$—O—$R_2$, wherein $R_1$ represents a branched alkyl(ene) residue with 10 carbon atoms, wherein at least one branching is located at position 1, 2, 3 or 4 to the oxygen atom $R_2$ represents a linear or branched alkyl(ene) residue with 1 to 13 carbon atoms and $R_1$ and $R_2$ are selected so that the total number of carbon atoms in formula (I) is 11 to 23.

A preferred embodiment of the invention relates to compounds of formula (I) in which $R_1$ is selected from the group consisting of 2-propylheptyl-, 3-methyl-2-propyl-hexyl, 4-methyl-2-propyl-hexyl and 5-methyl-2-propyl-hexyl-, trimethylheptyl-, 3,5-dimethyloctyl-, 2,2-dimethyloctyl-, 1-ethyl-octyl-, 2-ethyl-octyl, 3-ethyl-octyl-, 4-ethyl-octyl-, 1-propyl-heptyl-, 3-propyl-heptyl- and 4-propyl-heptyl-.

The compounds of formula (I) are especially preferred in which $R_1$ is selected from the group consisting of 2-propyl-heptyl-, 3-methyl-2-propyl-hexyl, 4-methyl-2-propyl-hexyl and 5-methyl-2-propyl-hexyl-.

Compounds of general formula (I) in which $R_1$ represents a 2-propylheptyl residue are especially preferred. These compounds accordingly correspond to the following formula:

2-propyl-heptyl-O—$R_2$, wherein $R_2$ represents a linear or branched alkyl(ene) residue with 1 to 13 carbon atoms and $R_1$ and $R_2$ are selected so that the total number of carbon atoms in formula (I) is 11 to 23.

A preferred compound is 2-propyl-heptyl-methyl ether, the compound of the following formula:

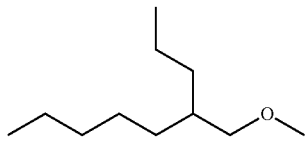

A preferred compound is 2-propyl-heptyl-ethyl ether, the compound of the following formula:

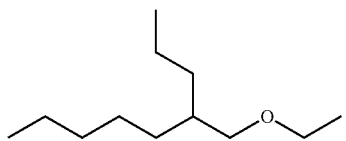

A preferred compound is 2-propyl-heptyl-butyl ether, the compound of the following formula:

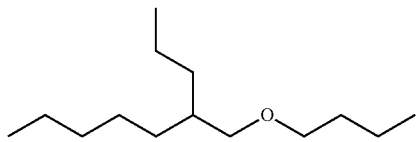

A preferred embodiment of the invention relates to compounds of formula (I) in which $R_1$ and $R_2$ represent a 2-propylheptyl residue. This compound accordingly corresponds to the following formula (=di(2-propylheptyl)ether):

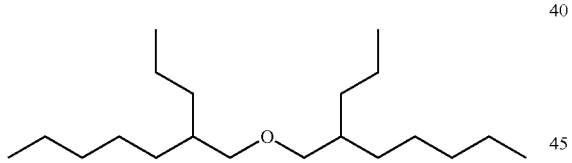

As well as the individual compounds of general formula (I), also any mixtures of two or more compounds of formula (I) are included, wherein especially mixtures of compounds of formula (I) in which $R_1$ is selected from the group consisting of 2-propylheptyl-, 3-methyl-2-propyl-hexyl, 4-methyl-2-propyl-hexyl and/or 5-methyl-2-propyl-hexyl- are preferred. Among the mixtures, those are preferred that have more than 50 wt % of 2-propylheptyl ethers, and preferably more than 80 wt % and preferably more than 90 wt %. 2-Propyl-heptyl ether means in this context a compound of formula (I) in which $R_1$ stands for a 2-propylheptyl residue, and preferably a compound of general formula (I) in which both $R_1$ and $R_2$ denote a 2-propylheptyl residue. These preferred mixtures comprise yet other compounds of formula (I), in which $R_1$ stands for 3-methyl-2-propyl-hexyl, 4-methyl-2-propyl-hexyl and/or 5-methyl-2-propyl-hexyl residues. These compounds are then preferably comprised in the mixtures in amounts of less than 50 wt %, less than 20 wt % and especially less than 10 wt %.

The following table lists further preferred compounds, together with the compounds already mentioned.

| No. | $R_1 =$ | $R_2 =$ |
|---|---|---|
| | 2-propyl-heptyl- | methyl- |
| | 2-propyl-heptyl- | ethyl- |
| | 2-propyl-heptyl- | n-propyl- |
| | 2-propyl-heptyl- | 2-methyl-ethyl- |
| | 2-propyl-heptyl- | 1-propenyl- |
| | 2-propyl-heptyl- | 2-propenyl- |
| | 2-propyl-heptyl- | n-butyl- |
| | 2-propyl-heptyl | but-1-enyl- |
| | 2-propyl-heptyl | but-2-enyl- |
| | 2-propyl-heptyl | but-3-enyl- |
| | 2-propyl-heptyl | 1-methyl-propyl- |
| | 2-propyl-heptyl | 2-methyl-propyl- |
| | 2-propyl-heptyl | 1,1-dimethylethyl- |
| | 2-propyl-heptyl- | n-pentyl- |
| | 2-propyl-heptyl- | 1-pentenyl- |
| | 2-propyl-heptyl- | 2-pentenyl- |
| | 2-propyl-heptyl- | 3-pentenyl- |
| | | 4-pentenyl- |
| | 2-propyl-heptyl- | 1-methylbutyl- |
| | 2-propyl-heptyl- | 2-methylbutyl- |
| | 2-propyl-heptyl- | 3-methylbutyl- |
| | 2-propyl-heptyl- | 1-ethylpropyl- |
| | 2-propyl-heptyl- | 1,1-dimethylpropyl- |
| | 2-propyl-heptyl- | 1,2-dimethylpropyl- |
| | 2-propyl-heptyl- | 2,2-dimethylpropyl- |
| | 2-propyl-heptyl- | n-hexyl- |
| | 2-propyl-heptyl- | 1-hexenyl- |
| | 2-propyl-heptyl- | 2-hexenyl- |
| | 2-propyl-heptyl- | 3-hexenyl- |
| | 2-propyl-heptyl- | 4-hexenyl- |
| | 2-propyl-heptyl- | 5-hexenyl- |
| | 2-propyl-heptyl- | 1-methylpentyl- |
| | 2-propyl-heptyl- | 2-methylpentyl- |
| | 2-propyl-heptyl- | 3-methylpentyl- |
| | 2-propyl-heptyl- | 4-methylpentyl- |
| | 2-propyl-heptyl- | 1-ethylbutyl- |
| | 2-propyl-heptyl- | 2-ethylbutyl- |
| | 2-propyl-heptyl- | 1,2-dimethylbutyl- |
| | 2-propyl-heptyl- | 1,3-dimethylbutyl- |
| | 2-propyl-heptyl- | 2,2-dimethylbutyl- |
| | 2-propyl-heptyl | 2,3-dimethylbutyl- |
| | 2-propyl-heptyl- | 3,3-dimethylbutyl- |
| | 2-propyl-heptyl- | n-heptyl- |
| | 2-propyl-heptyl- | 1-heptenyl- |
| | 2-propyl-heptyl- | 2-heptenyl- |
| | 2-propyl-heptyl- | 3-heptenyl- |
| | 2-propyl-heptyl- | 4-heptenyl- |
| | 2-propyl-heptyl- | 5-heptenyl- |
| | 2-propyl-heptyl- | 6-heptenyl- |
| | 2-propyl-heptyl- | 1-methyl-hexyl- |
| | 2-propyl-heptyl- | 2-methyl-hexyl- |
| | 2-propyl-heptyl- | 3-methyl-hexyl- |
| | 2-propyl-heptyl- | 4-methyl-hexyl- |
| | 2-propyl-heptyl- | 5-methyl-hexyl- |
| | 2-propyl-heptyl- | 1-ethyl-pentyl- |
| | 2-propyl-heptyl- | 2-ethyl-pentyl- |
| | 2-propyl-heptyl- | 3-ethyl-pentyl- |
| | 2-propyl-heptyl- | 4-ethyl-pentyl- |
| | 2-propyl-heptyl- | 1-propyl-butyl- |
| | 2-propyl-heptyl- | 2-propyl-butyl- |
| | 2-propyl-heptyl- | 3-propyl-butyl- |
| | 2-propyl-heptyl- | 1,1-dimethyl-pentyl- |
| | 2-propyl-heptyl- | 1,2-dimethyl-pentyl- |
| | 2-propyl-heptyl- | 1,3-dimethyl-pentyl- |
| | 2-propyl-heptyl- | 1,4-dimethyl-pentyl- |
| | 2-propyl-heptyl- | 2,2-dimethyl-pentyl- |
| | 2-propyl-heptyl- | 2,3-dimethyl-pentyl- |
| | 2-propyl-heptyl- | 2,4-dimethyl-pentyl- |
| | 2-propyl-heptyl- | 1,1,2 trimethyl-butyl- |
| | 2-propyl-heptyl- | 1,2,3-trimethylbutyl- |
| | 2-propyl-heptyl- | 1-methyl-2-ethyl-butyl- |
| | 2-propyl-heptyl- | n-octyl- |
| | 2-propyl-heptyl- | 1-octenyl- |
| | 2-propyl-heptyl- | 2-octenyl- |
| | 2-propyl-heptyl- | 3-octenyl- |

| No. | R₁ = | R₂ = |
|---|---|---|
| | 2-propyl-heptyl- | 4-octenyl- |
| | 2-propyl-heptyl- | 5-octenyl- |
| | 2-propyl-heptyl- | 1-methyl-heptyl- |
| | 2-propyl-heptyl- | 2-methyl-heptyl- |
| | 2-propyl-heptyl- | 3-methyl-heptyl- |
| | 2-propyl-heptyl- | 4-methyl-heptyl- |
| | 2-propyl-heptyl- | 5-methyl-heptyl- |
| | 2-propyl-heptyl- | 6-methyl-heptyl- |
| | 2-propyl-heptyl- | 1-ethyl-hexyl- |
| | 2-propyl-heptyl- | 2-ethyl-hexyl- |
| | 2-propyl-heptyl- | 3-ethyl-hexyl- |
| | 2-propyl-heptyl- | 4-ethyl-hexyl- |
| | 2-propyl-heptyl- | 1-propyl-pentyl- |
| | 2-propyl-heptyl- | 2-propyl-pentyl- |
| | 2-propyl-heptyl- | 3-propyl-pentyl- |
| | 2-propyl-heptyl- | 1-butyl-butyl- |
| | 2-propyl-heptyl- | 2-butyl-butyl- |
| | 2-propyl-heptyl- | 3-butyl-butyl- |
| | 2-propyl-heptyl- | 1,1-dimethyl-hexyl- |
| | 2-propyl-heptyl- | 1,2-dimethyl-hexyl- |
| | 2-propyl-heptyl- | 1,3-dimethyl-hexyl- |
| | 2-propyl-heptyl- | 1,4-dimethyl-hexyl- |
| | 2-propyl-heptyl- | 2,2-dimethyl-hexyl- |
| | 2-propyl-heptyl- | 2,3-dimethyl-hexyl- |
| | 2-propyl-heptyl- | 2,4-dimethyl-hexyl- |
| | 2-propyl-heptyl- | 1,1,2-trimethyl-pentyl- |
| | 2-propyl-heptyl- | 1,2,3-trimethylpentyl- |
| | 2-propyl-heptyl- | 2,4,4-trimethyl-pentyl- |
| | 2-propyl-heptyl- | 1-methyl-2-ethyl-pentyl- |
| | 2-propyl-heptyl- | 1,1,3,3-tetramethyl-butyl- |
| | 2-propyl-heptyl- | n-nonyl- |
| | 2-propyl-heptyl- | 1-nonenyl- |
| | 2-propyl-heptyl- | 2-noneyl- |
| | 2-propyl-heptyl- | 3-noneyl- |
| | 2-propyl-heptyl- | 4-noneyl- |
| | 2-propyl-heptyl- | 5-noneyl- |
| | 2-propyl-heptyl- | 6-noneyl- |
| | 2-propyl-heptyl- | 7-noneyl- |
| | 2-propyl-heptyl- | 8-noneyl- |
| | 2-propyl-heptyl- | 1-methyl-octyl- |
| | 2-propyl-heptyl- | 2-methyl-octyl- |
| | 2-propyl-heptyl- | 3-methyl-octyl- |
| | 2-propyl-heptyl- | 4-methyl-octyl- |
| | 2-propyl-heptyl- | 5-methyl-octyl- |
| | 2-propyl-heptyl- | 6-methyl-octyl- |
| | 2-propyl-heptyl- | 7-methyl-octyl- |
| | 2-propyl-heptyl- | 1-ethyl-heptyl- |
| | 2-propyl-heptyl- | 2-ethyl-heptyl- |
| | 2-propyl-heptyl- | 3-ethyl-heptyl- |
| | 2-propyl-heptyl- | 4-ethyl-heptyl- |
| | 2-propyl-heptyl- | 5-ethyl-heptyl- |
| | 2-propyl-heptyl- | 6-ethyl-heptyl- |
| | 2-propyl-heptyl- | 1-propyl-hexyl- |
| | 2-propyl-heptyl- | 2-propyl-hexyl- |
| | 2-propyl-heptyl- | 3-propyl-hexyl- |
| | 2-propyl-heptyl- | 4-propyl-hexyl- |
| | 2-propyl-heptyl- | 5-propyl-hexyl- |
| | 2-propyl-heptyl- | 1-butyl-pentyl- |
| | 2-propyl-heptyl- | 2-butyl-pentyl- |
| | 2-propyl-heptyl- | 3-butyl-pentyl- |
| | 2-propyl-heptyl- | 1,1-dimethyl-heptyl- |
| | 2-propyl-heptyl- | 1,2-dimethyl-heptyl- |
| | 2-propyl-heptyl- | 1,3-dimethyl-heptyl- |
| | 2-propyl-heptyl- | 1,4-dimethyl-heptyl- |
| | 2-propyl-heptyl- | 2,2-dimethyl-heptyl- |
| | 2-propyl-heptyl- | 2,3-dimethyl-heptyl- |
| | 2-propyl-heptyl- | 2,4-dimethyl-heptyl- |
| | 2-propyl-heptyl- | 1,1,2 trimethyl-hexyl- |
| | 2-propyl-heptyl- | 1,2,3-trimethyl-hexyl- |
| | 2-propyl-heptyl- | 2-methyl-4,4-dimethyl-hexyl- |
| | 2-propyl-heptyl- | 3,5,5-trimethyl-hexyl- |
| | 2-propyl-heptyl- | 1-methyl-2-ethyl-hexyl- |
| | 2-propyl-heptyl- | decyl- |
| | 2-propyl-heptyl- | 1-decenyl- |
| | 2-propyl-heptyl- | 2-decenyl- |
| | 2-propyl-heptyl- | 3-decenyl- |
| | 2-propyl-heptyl- | 4-decenyl- |
| | 2-propyl-heptyl- | 1-propyl-heptyl- |
| | 2-propyl-heptyl- | 2-propylheptyl- |
| | 2-propyl-heptyl- | 3-propyl-heptyl- |
| | 2-propyl-heptyl- | 4-propyl-heptyl- |
| | 2-propyl-heptyl- | 1-ethyl-octyl- |
| | 2-propyl-heptyl- | 2-ethyl-octyl- |
| | 2-propyl-heptyl- | 3-ethyl-octyl- |
| | 2-propyl-heptyl- | 4-ethyl-octyl- |
| | 2-propyl-heptyl- | 3-methyl-2-propyl-hexyl- |
| | 2-propyl-heptyl- | 4-methyl-2-propyl-hexyl- |
| | 2-propyl-heptyl- | 5-methyl-2-propyl-hexyl- |
| | 2-propyl-heptyl- | trimethylheptyl- |
| | 2-propyl-heptyl- | 3,5-dimethyloctyl- |
| | 2-propyl-heptyl- | 2,2-dimethyloctyl- |
| | 2-propyl-heptyl- | undecyl- |
| | 2-propyl-heptyl- | 1-undecenyl- |
| | 2-propyl-heptyl- | 2-undecenyl- |
| | 2-propyl-heptyl- | 3-undecenyl- |
| | 2-propyl-heptyl- | 4-undecenyl- |
| | 2-propyl-heptyl- | 1-methyl-decyl- |
| | 2-propyl-heptyl- | 2-methyl-decyl- |
| | 2-propyl-heptyl- | 3-methyl-decyl- |
| | 2-propyl-heptyl- | 4-methyl-decyl- |
| | 2-propyl-heptyl- | 1-ethyl-nonyl- |
| | 2-propyl-heptyl- | 2-ethyl-nonyl- |
| | 2-propyl-heptyl- | 3-ethyl-nonyl- |
| | 2-propyl-heptyl- | 4-ethyl-nonyl- |
| | 2-propyl-heptyl- | 1-propyl-octyl- |
| | 2-propyl-heptyl- | 2-propyl-octyl- |
| | 2-propyl-heptyl- | 3-propyl-octyl- |
| | 2-propyl-heptyl- | 4-propyl-octyl- |
| | 2-propyl-heptyl- | dodecyl- |
| | 2-propyl-heptyl- | 1-dodecenyl- |
| | 2-propyl-heptyl- | 2-dodecenyl- |
| | 2-propyl-heptyl- | 3-dodecenyl- |
| | 2-propyl-heptyl- | 4-dodecenyl- |
| | 2-propyl-heptyl- | 5-dodecenyl- |
| | 2-propyl-heptyl- | 1-ethyl-decyl- |
| | 2-propyl-heptyl- | 2-ethyl-decyl- |
| | 2-propyl-heptyl- | 3-ethyl-decyl- |
| | 2-propyl-heptyl- | 4-ethyl-decyl- |
| | 2-propyl-heptyl- | 1-butyl-octyl- |
| | 2-propyl-heptyl- | 2-butyl-octyl- |
| | 2-propyl-heptyl- | 3-butyl-octyl- |
| | 2-propyl-heptyl- | 4-butyl-octyl- |
| | 2-propyl-heptyl- | 2-hexyl-hexyl- |
| | 2-propyl-heptyl- | 2,5,8-trimethyl-nonyl |
| | 2-propyl-heptyl- | 2,2,4,6,6-pentamethylheptyl |
| | 2-propyl-heptyl- | tridecyl- |
| | 2-propyl-heptyl- | 1-tridecenyl- |
| | 2-propyl-heptyl- | 2-tridecenyl- |
| | 2-propyl-heptyl- | 3-tridecenyl- |
| | 2-propyl-heptyl- | 4-tridecenyl- |
| | 2-propyl-heptyl- | 5-tridecenyl- |
| | 2-propyl-heptyl- | 1-methyl-dodecyl- |
| | 2-propyl-heptyl- | 2-methyl-dodecyl- |
| | 2-propyl-heptyl- | 3-methyl-dodecyl- |
| | 2-propyl-heptyl- | 4-methyl-dodecyl- |
| | 2-propyl-heptyl- | 1-ethyl-undecyl- |
| | 2-propyl-heptyl- | 2-ethyl-undecyl- |
| | 2-propyl-heptyl- | 3-ethyl-undecyl- |
| | 2-propyl-heptyl- | 4-ethyl-undecyl- |
| | 2-propyl-heptyl- | 1-propyl-decyl- |
| | 2-propyl-heptyl- | 2-propyl-decyl- |
| | 2-propyl-heptyl- | 3-propyl-decyl- |
| | 2-propyl-heptyl- | 4-propyl-decyl- |
| | 2-propyl-heptyl- | tetramethyl-nonyl [=isotridecyl-] |
| | 2-propyl-heptyl- | tetradecyl- |
| | 2-propyl-heptyl- | 1-tetradecenyl- |
| | 2-propyl-heptyl- | 2-tetradecenyl- |
| | 2-propyl-heptyl- | 3-tetradecenyl- |
| | 2-propyl-heptyl- | 4-tetradecenyl- |
| | 2-propyl-heptyl- | 5-tetradecenyl- |
| | 2-propyl-heptyl- | 6-tetradecenyl- |
| | 2-propyl-heptyl- | 1-ethyl-dodecyl- |
| | 2-propyl-heptyl- | 2-ethyl-dodecyl- |
| | 2-propyl-heptyl- | 3-ethyl-dodecyl- |

-continued

| No. | $R_1 =$ | $R_2 =$ |
|-----|---------|---------|
|     | 2-propyl-heptyl- | 4-ethyl-dodecyl- |
|     | 2-propyl-heptyl- | 1-butyl-decyl- |
|     | 2-propyl-heptyl- | 2-butyl-decyl- |
|     | 2-propyl-heptyl- | 3-butyl-decyl- |
|     | 2-propyl-heptyl- | 4-butyl-decyl- |
|     | 2-propyl-heptyl- | 1-hexyl-octyl- |
|     | 2-propyl-heptyl- | 2-hexyl-octyl- |
|     | 2-propyl-heptyl- | 3-hexyl-octyl- |
|     | 2-propyl-heptyl- | 4-hexyl-octyl- |

Cosmetic/Pharmaceutical Preparations

Surprisingly, the compounds according to the invention are particularly suitable for cosmetic and/or pharmaceutical preparations, especially for preparations for which a "light" feel on the skin is important. The compounds can be incorporated very well in various formulations. They have a sensory profile that is comparable to that of volatile silicones, for example cyclomethicones. They display improved skin compatibility compared to known dialkyl ethers.

According to the invention, a single compound according to claim 1 or any mixture of different compounds according to claim 1 can be used.

One aspect of the invention therefore relates to the use of one or more compounds of general formula (I)

$R_1$—O—$R_2$, wherein $R_1$ represents a branched alkyl(ene) residue with 10 to 22 carbon atoms, wherein at least one branching is located at position 1, 2, 3 or 4 to the oxygen atom $R_2$ represents a linear or branched alkyl(ene) residue with 1 to 13 carbon atoms and $R_1$ and $R_2$ are selected so that the total number of carbon atoms in formula (I) is 11 to 23, for the production of or in cosmetic and/or pharmaceutical preparations, especially as oily substances and/or as solubilizers and/or as dispersing agents in cosmetic and/or pharmaceutical preparations. Preferably those compounds or mixtures thereof are used that were described in the preceding sections. Especially preferably, compounds of formula (I) are used in which $R_1$ stands for a 2-propylheptyl residue, or mixtures of ethers of general formula (I) in which these 2-propylheptyl ethers are comprised.

A further aspect of the invention is in particular the use of the compounds according to formula (I) in cosmetic and/or pharmaceutical preparations for wetting or impregnating or coating household cleaning wipes and/or personal hygiene wipes, which are used for body cleansing and/or for body care.

The present invention further relates to cosmetic and/or pharmaceutical preparations comprising, in a cosmetically and/or pharmaceutically suitable vehicle, 0.1 to 95 wt % of one or more compounds according to one of claims 1 to 5.

The present invention further relates to cosmetic and/or pharmaceutical preparations comprising
(a) at least one compound according to claims 1 to 5
(b) at least one surface-active substance (b-1) and/or wax component (b-2) and/or polymer (b-3) and/or a further oily substance (b-4)

The present invention further relates to cosmetic and/or pharmaceutical preparations comprising
(a) at least one compound according to claims 1 to 5
(d) at least one UV-light protection filter Cosmetic and/or pharmaceutical preparations are preferred that contain
(a) at least one compound of general formula (I)

$R_1$—O—$R_2$, wherein $R_1$ represents a branched alkyl(ene) residue with 10 carbon atoms, wherein at least one branching is located at position 1, 2, 3 or 4 to the oxygen atom $R_2$ represents a linear or branched alkyl(ene) residue with 1 to 13 carbon atoms and $R_1$ and $R_2$ are selected so that the total number of carbon atoms in formula (I) is 11 to 23.

(b) at least one surface-active substance (b-1) and/or wax component (b-2) and/or polymer (b-3) and/or a further oily substance (b-4)

A preferred embodiment of the invention relates to cosmetic and/or pharmaceutical preparations comprising
(a) at least one compound of general formula (I)

$R_1$—O—$R_2$, wherein $R_1$ represents a branched alkyl(ene) residue, selected from the group consisting of 2-propylheptyl-, 3-methyl-2-propyl-hexyl, 4-methyl-2-propyl-hexyl and 5-methyl-2-propyl-hexyl-, trimethylheptyl-, 3,5-dimethyloctyl-, 2,2-dimethyloctyl-, 1-ethyl-octyl-, 2-ethyl-octyl, 3-ethyl-octyl-, 4-ethyl-octyl-, 1-propyl-heptyl-, 3-propyl-heptyl- and 4-propyl-heptyl- $R_2$ represents a linear or branched alkyl(ene) residue with 1 to 13 carbon atoms and $R_1$ and $R_2$ are selected so that the total number of carbon atoms in formula (I) is 11 to 23.

(b) at least one emulsifier (b-1) and/or surfactant (b-2) and/or wax component (b-3) and/or polymer (b-4) and/or a further oily substance (b-5)

Cosmetic and/or pharmaceutical preparations are especially preferred that contain
(a) at least one compound of general formula (I)

$R_1$—O—$R_2$, wherein $R_1$ represents a 2-propylheptyl residue $R_2$ represents a linear or branched alkyl(ene) residue with 1 to 13 carbon atoms and $R_1$ and $R_2$ are selected so that the total number of carbon atoms in formula (I) is 11 to 23.

(b) at least one emulsifier (b-1) and/or surfactant (b-2) and/or wax component (b-3) and/or polymer (b-4) and/or a further oily substance (b-5)

The preparations according to the invention preferably comprise 0.1 to 95, especially 0.2 to 80 wt %, especially 0.5 to 70, preferably 0.75 to 60 wt %, especially 1 to 50 wt %, preferably 1-40 wt % of at least one compound according to formula (I).

The invention further relates to cosmetic and/or pharmaceutical preparations comprising
a) 0.1-95 wt %, especially 0.2 to 80 wt %, especially 0.1 to 70, preferably 0.1 to 60, especially 0.1 to 50 wt %, preferably 0.1-40 wt % of at least one compound according to claim 1,
b) 0.1-20 wt % of surface-active substance (b-1) and/or wax component (b-2) and/or polymer (b-3), 0.1-40 wt % of further oily substances (b-4) and
c) 0-98 wt % water.

The preparations according to the invention preferably comprise at least 0.1, especially at least 0.5, especially at least 0.75, preferably at least 1, preferably at least 5 wt % of one or more compounds according to claim 1.

All percentages by weight refer to percentage by weight relative to the cosmetic and/or pharmaceutical preparation.

The preparations according to the invention, and the compounds according to the invention of general formula (I) are suitable as a base for incorporation in all cosmetic products for body care and cleaning, e.g. body oil, baby oil, body milk, creams, lotions, sprayable emulsions, sunscreens, antiperspirants, liquid soaps and bars of soap etc. They can also be used in surfactant-comprising preparations such as e.g. foam baths and shower gels, hair shampoos and rinses. They can be applied as care component on tissues, papers, wipes, nonwoven products, sponges, puffs, plasters and bandages, which find application in the area of hygiene and care (moist wipes for baby hygiene and baby care, cleaning wipes, face-cleaning wipes, skin-care wipes, care wipes with active substances against skin aging, wipes with sunscreen formulations and insect repellents and wipes for decorative cosmetics or for after-sun treatment, toilet moist wipes, antiperspirant wipes, diapers, handkerchiefs, wet wipes, hygiene products, selftanning wipes). They can also be used in, among other things, preparations for hair care, hair cleaning or hair coloring. Furthermore, they can be used in preparations for decorative cosmetics, such as for example lipsticks, lipgloss, makeup, foundations, powders, eye shadow, mascara and the like.

Depending on the intended application, the cosmetic formulations comprise a number of other auxiliary ingredients and additives, such as for example surfactants, further oily substances, emulsifiers, nacreous waxes, consistency additives, thickening agents, overfatting agents, stabilizers, polymers, fats, waxes, lecithins, phospholipids, biogenic active substances, UV-light protection factors, antioxidants, deodorants, antiperspirants, antidandruff agents, film-forming agents, swelling agents, insect repellents, selftanning agents, tyrosinase inhibitors (depigmenting agents), fillers, hydrotropes, solubilizers, preservatives, perfume oils, dyes etc., examples of which are listed below.

Surface-Active Substance b-1)

In one embodiment of the invention, the preparations according to the invention comprise at least one surface-active substance. The preparations according to the invention comprise the surface-active substance(s) in an amount from 0 to 80 wt %, especially 0 to 40 wt %, preferably 0.1 to 20 wt %, preferably 0.1 to 15 wt % and especially 0.1 to 10 wt % relative to the total weight of the preparation.

In principle, any substance that lowers the surface tension between the aqueous and the nonaqueous phase is suitable as surface-active substance. Surface-active substances comprise emulsifiers and surfactants.

In one embodiment of the invention, the preparation according to the invention comprises more than one surface-active substance. A person skilled in the art uses usual systems (e.g. emulsifiers and coemulsifiers) depending on the other components.

A suitable emulsifier is in principle any surface-active substance, but especially substances with an HLB value from 1 to 20 on the Griffin scale. Each emulsifier is assigned a so-called HLB value (a dimensionless number between 1 and 20, Griffin scale), which shows whether there is preferential water or oil solubility. Numbers under 9 characterize preferably oil-soluble, hydrophobic emulsifiers, numbers over 11 characterize water-soluble, hydrophilic emulsifiers. The HLB value says something about the equilibrium of the size and strength of the hydrophilic and of the lipophilic groups of an emulsifier. The Griffin scale is described in W. C. Griffin, J. Soc. Cosmet. Chem. 1 (1949) 311; W. C. Griffin, J. Soc. Cosmet. Chem. 5 (1954) 249.

The HLB value of an emulsifier can also be calculated from increments, wherein the HLB-increments for the various hydrophilic and hydrophobic groups that make up a molecule can be found from published tables (e.g. H. P. Fiedler, Lexikon der Hilfsstoffe für Pharmazie, Kosmetik and angrenzende Gebiete [Dictionary of excipients for pharmacy, cosmetics and related areas], Editio Cantor Verlag, Aulendorf, 4th Ed., 1996) or the manufacturer's data. In practice, the solubility of the emulsifier in the two phases determines the type of emulsion. If the emulsifier is more soluble in water, an O/W emulsion is obtained. If, on the other hand, the emulsifier has better solubility in the oil phase, a W/O emulsion is formed under otherwise identical conditions of preparation.

Nonionic Emulsifiers

The group of nonionic emulsifiers includes for example:
(1) Adducts of 2 to 50 mol ethylene oxide and/or 1 to 20 mol propylene oxide on linear fatty alcohols with 8 to 40 carbon atoms, on fatty acids with 12 to 40 carbon atoms and on alkyl phenols with 8 to 15 carbon atoms in the alkyl group.
(2) $C_{12}$-$C_{18}$ fatty acid mono- and diesters of adducts of 1 to 50 mol ethylene oxide on glycerol.
(3) Sorbitan mono- and diesters of saturated and unsaturated fatty acids with 6 to 22 carbon atoms and ethylene oxide adducts thereof.
(4) Alkyl mono- and oligoglycosides with 8 to 22 carbon atoms in the alkyl residue and ethoxylated analogs thereof.
(5) Adducts of 7 to 60 mol ethylene oxide on castor oil and/or hydrogenated castor oil.
(6) Polyol- and especially polyglycerol esters, e.g. polyolpoly-12-hydroxystearates, polyglycerol polyricinoleate, polyglyceryl-4-laurates, polyglycerol diisostearate or polyglycerol dimerate. Mixtures of compounds from several of these classes of substances are also suitable, e.g. polyglyceryl-4 diisostearates/polyhydroxystearates/sebacates.
(7) Adducts of 2 to 15 mol ethylene oxide on castor oil and/or hydrogenated castor oil.
(8) Partial esters based on linear, branched, unsaturated or saturated $C_6$-$C_{22}$ fatty acids, ricinoleic acid and 12-hydroxystearic acid and polyglycerol, pentaerythritol, dipentaerythritol, sugar alcohols (e.g. sorbitol), alkyl glucosides (e.g. methylglucoside, butylglucoside, laurylglucoside) and polyglucosides (e.g. cellulose), or mixed esters, and sucrose polystearate (commercially available as Emulgade® SUCRO, Cognis GmbH).
(9) Polysiloxane-polyalkyl-polyether copolymers or corresponding derivatives.
(10) Mixed esters from pentaerythritol, fatty acids, citric acid and fatty alcohol and/or mixed esters of fatty acids with 6 to 22 carbon atoms, methylglucose and polyols, preferably glycerol or polyglycerol.

The adducts of ethylene oxide and/or of propylene oxide on fatty alcohols, fatty acids, alkyl phenols, glycerol mono- and diesters and sorbitan mono- and diesters of fatty acids or on castor oil are known, commercially available products. They are mixtures of homologs whose average degree of alkoxylation corresponds to the proportions of the amounts of ethylene oxide and/or propylene oxide and substrate, with which the reaction of adduct formation is carried out. They are W/O or O/W emulsifiers, depending on the degree of ethoxylation. $C_{12/18}$ fatty acid mono- and diesters of adducts of ethylene oxide on glycerol are known refatting agents for cosmetic preparations.

According to the invention, particularly suitable and mild emulsifiers are polyolpoly-12-hydroxystearates and mixtures thereof, which are sold for example under the brand names "Dehymuls® PGPH" (W/O emulsifier) or "Eumulgin® VL 75" (mixture with coconut glucosides in the weight ratio 1:1, O/W emulsifier) or Dehymuls® SBL (W/O emulsifier) by Cognis Deutschland GmbH. In this connection, reference may be made in particular to European patent EP 766 661 B1. The polyol component of these emulsifiers can be derived from substances that have at least two, preferably 3 to 12 and especially 3 to 8 hydroxyl groups and 2 to 12 carbon atoms.

In principle, emulsifiers with an HLB value from 1 to 8, which are listed in numerous published tables and are known by a person skilled in the art, are suitable as lipophilic W/O emulsifiers. Some of these emulsifiers are listed for example in Kirk-Othmer, "Encyclopedia of Chemical Technology", 3rd Ed., 1979, Vol. 8, page 913. For ethoxylated products, the HLB value can also be calculated from the following formula: HLB=(100−L): 5, where L is the proportion by weight of the lipophilic groups, i.e. the fatty alkyl or fatty acyl groups in percentage by weight, in the ethylene oxide adducts.

Particularly advantageous, from the group of W/O emulsifiers, are partial esters of polyols, especially of $C_4$-$C_6$ polyols, for example partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and industrial-grade mixtures thereof. Adducts of 1 to 30, preferably 5 to 10 mol ethylene oxide on the stated sorbitan esters are also suitable as emulsifiers.

Depending on the formulation, it may be advantageous to use in addition at least one emulsifier from the group of nonionic O/W emulsifiers (HLB value: 8-18) and/or solubilizers. These are for example the ethylene oxide adducts already mentioned at the beginning with a correspondingly high degree of ethoxylation, e.g. 10-20 ethylene oxide units for O/W emulsifiers and 20-40 ethylene oxide units for so-called solubilizers. Ceteareth-12, Ceteareth-20 and PEG-20 stearate are especially advantageous as O/W emulsifiers according to the invention. Eumulgin® HRE 40 (INCI: PEG-40 Hydrogenated Castor Oil), Eumulgin® HRE 60 (INCI: PEG-60 Hydrogenated Castor Oil), Eumulgin® L (INCI: PPG-1-PEG-9 Laurylglycolether), and Eumulgin® SML 20 (INCI: Polysorbate-20) are preferred as suitable solubilizers.

Non-ionic emulsifiers from the group of alkyl oligoglycosides are particularly skin-compatible and therefore preferred as suitable O/W emulsifiers. $C_8$-$C_{22}$ alkyl mono- and oligoglycosides, the production and the use thereof are known from the prior art. They are produced in particular by reaction of glucose or oligosaccharides with primary alcohols with 6 to 24, preferably 8 to 22 carbon atoms. Regarding the glycoside residue, both monoglycosides, in which a cyclic sugar residue is attached by a glycosidic bond to the fatty alcohol, and oligomeric glycosides with a degree of oligomerization preferably up to about 8, are suitable. The degree of oligomerization is a statistical average, based on a distribution of homologs that is usual for these industrial products. Products that are available under the designation Plantacare® or Plantaren® comprise a $C_8$-$C_{16}$ alkyl group attached by a glucosidic bond to an oligoglucoside residue, whose average degree of oligomerization is 1 to 2. The acyl glucamides derived from glucamine are also suitable as nonionic emulsifiers. A product that is sold under the designation Emulgade® PL 68/50 by Cognis Deutschland GmbH and is a 1:1 mixture of alkyl polyglucosides and fatty alcohols, is preferred according to the invention. A mixture of lauryl glucosides, polyglyceryl-2-dipolyhydroxystearates, glycerol and water, which is marketed under the designation Eumulgin® VL 75, can also be used advantageously according to the invention.

Moreover, substances such as lecithins and phospholipids may come into consideration as emulsifiers. As examples of natural lecithins, we may mention the kephalins, which are also called phosphatide acids and are derivatives of 1,2-diacyl-sn-glycerin-3-phosphoric acids. Moreover, phospholipids are usually understood to be mono- and preferably diesters of phosphoric acid with glycerol (glycerol phosphates), which are generally classed as fats. In addition, sphingosines or sphingolipids may also be considered.

Silicone emulsifiers, for example, can be present as emulsifiers. These can be selected for example from the group of alkyl methicone copolyols and/or alkyl dimethicone copolyols, especially from the group of compounds that are characterized by the following chemical structure:

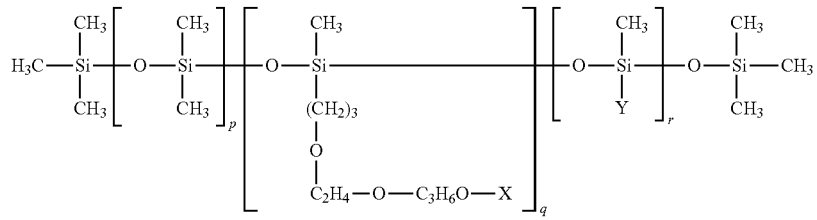

in which X and Y are selected independently of one another from the group H (hydrogen) and the branched and unbranched alkyl groups, acyl groups and alkoxy groups with 1-24 carbon atoms, p represents a number from 0 to 200, q represents a number from 1 to 40, and r represents a number from 1 to 100.

An example of silicone emulsifiers that can be used especially advantageously in the sense of the present invention are dimethicone copolyols, which are sold by Evonik Goldschmidt under the trademarks AXIL® B 8842, ABIL® B 8843, ABIL® B 8847, ABIL® B 8851, ABIL® B 8852, ABIL® B 8863, ABIL® B 8873 and ABIL® B 88183.

Another example of surface-active substances that can be used especially advantageously in the sense of the present invention is cetyl PEG/PPG-10/1 dimethicone (cetyl dimethicone copolyol), which is sold by Evonik Goldschmidt under the trademark ABIL® EM 90.

Another example of surface-active substances that can be used especially advantageously in the sense of the present invention is cyclomethicone dimethicone copolyol, which is sold by Evonik Goldschmidt under the trademark ABIL® EM 97 and ABIL® WE 09.

Furthermore, the emulsifier lauryl PEG/PPG-18/18 methicone (lauryl methicone copolyol), which is available from the company Dow Corning Ltd. under the trademark Dow Corning® 5200 Formulation Aid, has proved to be quite especially advantageous. A silicone emulsifier with the INCI name Cyclopentasiloxane and PEG/PG-18-18 Dimethicone, which is available for example under the trade name Dow Corning® 5225 C Formulation Aid, is also advantageous.

Another advantageous silicone emulsifier is octyl dimethicone ethoxy glucoside from the company Wacker. For a water-in-silicone oil emulsion according to the invention, it is possible to use all known emulsifiers that are used for this type of emulsion. Water-in-silicone emulsifiers that are especially preferred according to the invention are cetyl PEG/PPG-10/1 dimethicone and lauryl PEG/PPG-18/18 methicone [e.g. ABIL® EM 90 Evonik Goldschmidt), DC5200 Formulation Aid (Dow Corning)] and any mixtures of these two emulsifiers.

A suitable anionic O/W emulsifier is for example the product obtainable under the INCI name Disodium Cetearyl Sulfosuccinate (trade name Eumulgin® Prisma, Cognis GmbH).

Surfactants

In one embodiment of the invention, the preparations according to the invention comprise at least one surfactant as surface-active compounds. Anionic, nonionic, cationic and/or amphoteric or zwitterionic surfactants can be comprised as surface-active substances. Preferably at least one anionic surfactant is comprised in surfactant-comprising cosmetic preparations, such as for example shower gels, foam baths, shampoos etc.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid-N-alkyl glucamides, protein hydrolyzates (especially wheat-based plant products), polyol fatty acid esters, sugar esters, sorbitan esters, polysorbates and amine oxides. If the nonionic surfactants comprise polyglycol ether chains, these can have a conventional, but preferably a narrower distribution of homologs.

Zwitterionic surfactants are those surface-active compounds having at least one quaternary ammonium group and at least one —COO$^{(-)}$ or —SO$_3^{(-)}$ group in the molecule. Especially suitable zwitterionic surfactants are the so-called betaines such as N-alkyl-N,N-dimethylammonium glycinates, for example coconut alkyl dimethylammonium glycinate, N-acyl-aminopropyl-N,N-dimethylammonium glycinates, for example coconut acylaminopropyl dimethylammonium glycinate, and 2-alkyl-3-carboxylmethyl-3-hydroxyethylimidazoline with in each case 8 to 18 carbon atoms in the alkyl or acyl group and coconut acylaminoethylhydroxyethylcarboxymethyl glycinate. A preferred zwitterionic surfactant is the fatty acid amide derivative known by the INCI name Cocamidopropyl Betaine.

Ampholytic surfactants are also especially suitable as co-surfactants. Ampholytic surfactants are those surface active compounds which, in addition to a $C_8$-$C_{18}$ alkyl or acyl group, comprise at least one free amino group and at least one —COOH— or —SO$_3$H group in the molecule and are capable of internal salt formation. Examples of suitable ampholytic surfactants are N-alkylglycines, N-alkylpropionic acids, N-alkylaminobutyric acids, N-alkyliminodipropionic acids (for example commercially available under the trade name Dehyton® DC), N-hydroxyethyl-N-alkylamidopropylglycines, N-alkyltaurines, N-alkylsarcosines, 2-alkylaminopropionic acids and alkylaminoacetic acids with in each case about 8 to 18 carbon atoms in the alkyl group. Especially preferred ampholytic surfactants are N-coconut alkylaminopropionate, coconut acyl-aminoethylaminopropionate and $C_{12-18}$ acylsarcosine. Derivatives of N-alkyliminodipropionic acids are also suitable, such as for example N-lauryl-beta-iminopropionates, commercially available under the trade name Deriphat® 160 C. Amphoacetates are also suitable, e.g. cocoamphoacetates (e.g. Dehyton® MC) or cocoamphodiacetates (e.g. Dehyton® DC).

Anionic surfactants are characterized by a water-solubilizing, anionic group, e.g. a carboxylate, sulfate, sulfonate, citrate or phosphate group and a lipophilic residue. Skin-compatible anionic surfactants are known by a person skilled in the art in large numbers from relevant manuals and are commercially available. These are in particular alkyl sulfates in the form of their alkali, ammonium or alkanolammonium salts, alkyl ether sulfates, alkyl ether carboxylates, acyl isethionates, acyl sarcosinates, acyltaurines with linear alkyl or acyl groups with 12 to 18 carbon atoms and sulfosuccinates and acylglutamates in the form of their alkali or ammonium salts. Especially suitable anionic surfactants are glyceryl stearate citrate (e.g. commercially available under the trade name Imwitor® 370, Imwitor® 372P, Axol® C,62 or Dracorin® CE 614035) or glyceryl stearate lactate compounds. An example of a suitable alkyl sulfate is sodium cetearyl sulfate (trade name Lanette® E), and an example of a suitable phosphate is potassium cetyl phosphate (trade name Amphisol® K). An example of a suitable acyl glutamate is sodium stearoyl glutamate (trade name e.g. Eumulgin® SG). Another example of a suitable anionic surfactant is sodium lauryl glucose carboxylate (trade name Plantapon® LGC).

Quaternary ammonium compounds can be used in particular as cationic surfactants. Ammonium halides, especially chlorides and bromides, are preferred, such as alkyl trimethylammonium chlorides, dialkyl dimethylammonium chlorides and trialkyl methylammonium chlorides, e.g. cetyl trimethylammonium chloride, stearyl trimethylammonium chloride, distearyl dimethylammonium chloride, lauryl dimethylammonium chloride, lauryl dimethylbenzylammonium chloride and tricetyl methylammonium chloride. Suitable pseudocationic surfactants are for example stearyl aminopropyl dimethylamine (commercially available under the trade name Dehyquart® S18 or Incromine® SB or TegoAmide® S18). Furthermore, the quaternary ester compounds with very good biodegradability, such as for example the dialkylammonium methosulfates and methylhydroxyalkyl dialcoyloxyalkylammonium methosulfates marketed under the trademark Stepantex® and the corresponding products of the Dehyquart® series can be used as cationic surfactants. The designation "Esterquats" generally means quaternized fatty acid triethanolamine ester salts. They can impart a special soft feel to the preparations according to the invention. They are known substances, which are produced by the relevant methods of organic chemistry. Further cationic surfactants usable according to the invention are the quaternized protein hydrolyzates. Suitable cationic surfactants are for example dipalmitoylethyl hydroxyethylmonium methosulfate (trade name Dehyquart® C4046), distearoylethyl hydroxyethylmonium methosulfate (trade name Dehyquart® F75), dicocoylethyl hydroxyethylmonium methosulfate (trade name Dehyquart® L80), behentrimonium chloride (trade name Varisoft® BT), distearyl dimonium chloride (trade name Varisoft® TA 100), palmitamidopropyltrimonium chloride (trade name Varisoft® PATC).

Wax Component b-2)

In one embodiment of the invention, the preparations according to the invention comprise at least one wax component. The preparations according to the invention comprise the wax component(s) in an amount from 0 to 40 wt %, especially from 0 to 20 wt %, preferably 0.1 to 15 wt % and especially 0.1 to 10 wt % relative to the total weight of the preparation.

The term wax usually means all natural or synthetically produced substances and mixtures of substances with the following properties: they are of solid to brittle, hard consistency, coarse- to fine-crystalline, translucent to cloudy and they melt above 30° C. without decomposition. Just a little above the melting point they are already of low viscosity and non-stringy and display highly temperature-dependent consistency and solubility. A wax component or a mixture of wax components that melt at 30° C. or above can be used according to the invention.

Fats and fat-like substances with wax-like consistency can also be used according to the invention as waxes, provided they have the required melting point. These include, among others, fats (triglycerides), mono- and diglycerides, natural and synthetic waxes, fatty and waxy alcohols, fatty acids, esters of fatty alcohols and fatty acids and fatty acid amides or any mixtures of these substances.

Fats are understood as triacyl glycerols, i.e. the triple esters of fatty acids with glycerol. Preferably they comprise saturated, unbranched and unsubstituted fatty acid residues. Moreover, they can also be mixed esters, i.e. triple esters of glycerol with various fatty acids. So-called hardened fats and oils, which are obtained by partial hydrogenation, can be used according to the invention and are particularly suitable as consistency additives. Hardened vegetable fats and oils are preferred, e.g. hydrogenated castor oil, peanut oil, soybean oil, rape oil, rapeseed oil, cottonseed oil, soybean oil, sunflower oil, palm oil, palm kernel oil, linseed oil, almond oil, maize oil, olive oil, sesame oil, cocoa butter, shea butter and coconut oil.

Among others, the triple esters of glycerol with $C_{12}$-$C_{60}$ fatty acids and especially $C_{12}$-$C_{36}$ fatty acids are suitable. This includes hydrogenated castor oil, a triple ester of glycerol and a hydroxystearic acid, which is marketed for example under the designation Cutina HR. Glycerol tristearate, glycerol tribehenate (e.g. Syncrowax HRC), glycerol tripalmitate or the triglyceride mixtures known under the designation Syncrowax HGLC are also suitable, provided that the melting point of the wax component or of the mixture is 30° C. or above.

Mono- and diglycerides or mixtures of these partial glycerides can be used in particular according to the invention as wax components. The glyceride mixtures usable according to the invention include the products sold by Cognis Deutschland GmbH & Co. KG, Novata AB and Novata B (mixture of $C_{12}$-$C_{18}$ mono-, di- and triglycerides) and Cutina® HVG (hydrogenated vegetable glycerides) or Cutina® GMS (glyceryl stearate).

The fatty alcohols usable according to the invention as wax component include the $C_{12}$-$C_{50}$ fatty alcohols. The fatty alcohols can be obtained from natural fats, oils and waxes, such as for example myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Saturated unbranched fatty alcohols are preferred according to the invention. However, unsaturated, branched or unbranched fatty alcohols can also be used according to the invention as wax component, provided they have the required melting point. Fatty alcohol cuts, such as are obtained in the reduction of naturally occurring fats and oils, e.g. beef tallow, peanut oil, colza oil, cottonseed oil, soybean oil, sunflower oil, palm kernel oil, linseed oil, castor oil, maize oil, rape oil, sesame oil, cocoa butter and coconut oil, can also be used according to the invention. However, synthetic alcohols can also be used, e.g. the linear, even-numbered fatty alcohols from Ziegler synthesis (Alfols) or the partially branched alcohols from oxo synthesis (Dobanols). $C_{14}$-$C_{22}$ fatty alcohols, which are marketed for example by Cognis Deutschland GmbH under the designation Lanette 16 ($C_{16}$ alcohol), Lanette 14 ($C_{14}$ alcohol), Lanette O ($C_{16}$/$C_{18}$ alcohol) and Lanette 22 ($C_{18}$/$C_{22}$ alcohol), are especially preferably suitable according to the invention. Fatty alcohols give the preparations a drier feeling on the skin than triglycerides and are therefore preferred to the latter.

$C_{14}$-$C_{40}$ fatty acids or mixtures thereof can also be used as wax components. These include for example myristic, pentadecanoic, palmitic, margaric, stearic, nonadecanoic, arachidic, behenic, lignoceric, cerotic, melissic, erucic and elaeostearic acid and substituted fatty acids, e.g. 12-hydroxystearic acid, and the amides or monoethanolamides of the fatty acids, wherein this list is illustrative and in no way limiting.

For example natural plant waxes can be used according to the invention, such as candelilla wax, carnauba wax, japan wax, esparto grass wax, cork wax, guaruma wax, rice germ oil wax, sugarcane wax, ouricury wax, montan wax, sunflower wax, fruit waxes such as orange waxes, lemon waxes, grapefruit wax, bayberry wax and animal waxes, e.g. beeswax, shellac wax, spermaceti, wool wax and preen oil. In the sense of the invention it may be advantageous to use hydrogenated or hardened waxes. The natural waxes usable according to the invention also include the mineral waxes, e.g. ceresin and ozokerite or the petrochemical waxes, e.g. petrolatum, paraffin waxes and microwaxes. Chemically modified waxes, especially the hard waxes, e.g. montan ester waxes, sasol waxes and hydrogenated jojoba waxes can also be used as the wax component. The synthetic waxes that can be used according to the invention include for example wax-like polyalkylene waxes and polyethylene glycol waxes. Vegetable waxes are preferred according to the invention.

The wax component can also be selected from the group of wax esters from saturated and/or unsaturated, branched and/or linear alkane carboxylic acids and saturated and/or unsaturated, branched and/or linear alcohols, from the group of esters from aromatic carboxylic acids, dicarboxylic acids, tricarboxylic acids or hydroxycarboxylic acids (e.g. 12-hydroxystearic acid) and saturated and/or unsaturated, branched and/or linear alcohols, and moreover from the group of lactides of long-chain hydroxycarboxylic acids. Examples of these esters are the $C_{16}$-$C_{40}$ alkyl stearates, $C_{20}$-$C_{40}$ alkyl stearates (e.g. Kester Wax K82H), $C_{20}$-$C_{40}$ dialkyl esters of dimer acids, $C_{18}$-$C_{38}$ alkyl hydroxystearoyl stearates or $C_{20}$-$C_{40}$ alkyl erucates. Moreover, $C_{30}$-$C_{50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate can be used.

Polymers b-3)

In one embodiment of the invention, the preparations according to the invention comprise at least one polymer. The preparations according to the invention comprise the polymer(s) in an amount from 0 to 20 wt %, preferably 0.05 to 18 wt %, preferably 0.05 to 15 wt %, especially preferably 0.05 to 10 wt %, especially 0.1 to 1 wt % relative to the total weight of the preparations. In a preferred embodiment of the invention the preparations according to the invention comprise the polymer/the polymers in an amount from 0.1 to 5 wt %, especially 0.1 to 3 wt %, especially 0.1 to 2 wt % relative to the total weight of the preparation.

Suitable cationic polymers are for example cationic cellulose derivatives, e.g. a quaternized hydroxyethylcellulose, which is available under the designation polymer JR 400® from Amerchol, cationic starch, copolymers of diallylammonium salts and acrylamides, quaternized vinyl pyrrolidone/vinyl imidazole polymers, e.g. Luviquat® (BASF), condensation products of polyglycols and amines, quaternized collagen polypeptides, for example lauryldimonium hydroxy-propyl hydrolyzed collagen (Lamequat® L/Grünau), quaternized wheat polypeptides, polyethyleneimine, cationic silicone polymers, e.g. amidomethicones, copolymers of adipic acid and dimethylaminohydroxypropyl diethylenetriamine (Cartaretine®/Sandoz), copolymers of acrylic acid with dimethyldiallylammonium chloride (Merquat® 550/Chemviron), polyaminopolyamides, cationic chitin derivatives such as for example quaternized chitosan, optionally with microcrystalline distribution, condensation products from dihaloalkylene, e.g. dibromobutane with bis-dialkyl amines, e.g. bis-dimethylamino-1,3-propane, cationic guar gum, e.g. Jaguar® CBS, Jaguar® C-17, Jaguar® C-16 from the company Celanese, quaternized ammonium salt polymers, e.g. Mirapol® A-15, Mirapol® AD-1, Mirapol® AZ-1 from the company Miranol.

The following may be considered as anionic, zwitterionic, amphoteric and nonionic polymers, for example vinyl acetate/crotonic acid copolymers, vinyl pyrrolidone/vinyl acrylate copolymers, vinyl acetate/butyl maleate/isobornyl acrylate copolymers, methylvinyl ether/maleic acid anhydride copolymers and esters thereof, uncrosslinked and polyol-crosslinked polyacrylic acids, acrylamidopropyl trimethylammonium chloride/acrylate copolymers, octylacrylamide/methylmethacrylate/tert-butyl aminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Especially suitable anionic polymers are those with the INCI name carbomer, e.g. the Carbopol types 980, 980, 981, 1382, 2984, 5984 and the products available under the trade names Rheocare® C plus and Rheocare® 400. Other suitable anionic polymers are those with the INCI name Acrylates/C10-30 Alkyl Acrylate Crosspolymer (trade names e.g. Pemulen® TR, Pemulen® TR 2, Carbopol® Ultrez), Acrylates Copolymer (trade names e.g. Rheocare TTA, TTN, TTN-2), Acrylamide/Sodium Acrylate Copolymer (trade names e.g. Cosmedia® ATC), Sodium Polyacrylate (trade names e.g. Cosmedia® ATH, Cosmedia® SP), Polyacrylamides (trade names e.g. Sepigel® 305 or Sepigel® 501). Preferred anionic polymers are polyacrylic acid homo- and copolymers.

Other suitable polymers are Silicone Elastomer Gums, such as silicone elastomer mixtures, e.g. mixtures with the INCI names Cyclopentasiloxane (and) Dimethiconol (and) Dimethicone Crosspolymer (trade name Dow Corning® DC 9027), mixtures with the INCI name Isodecyl neopentanoate (and) Dimethicone/bis-isobutyl PPG-20 Crosspolymer (trade name Dow Corning® DC EL 8051 IN), mixtures with the INCI name Dimethicone/Vinyl Dimethicone Crosspolymer (and) C12-14 Pareth-12 (trade name Dow Corning® DC 9509) and mixtures with the INCI name Dimethicone/Vinyl Dimethicone Crosspolymer (and) Silica (trade name Dow Corning® DC 9701 Cosmetic Powder).

Polysaccharides are also suitable as polymers, in particular xanthan gum, guar gum, agar-agar, alginates and tyloses and tara gum, carrageenan, sclerotium gum and natural cellulose.

Further Oily Substances b-4)

Body-care products, such as creams, body oils, lotions and milks, usually comprise a number of further oily substances and emollients, which contribute to further optimization of the sensory properties. The oily substances (compounds according to the invention plus further oily substances) are usually comprised in a total amount of 0.1-80, especially 0.5 to 70, preferably 1 to 60, especially 1 to 50 wt %, especially 1 to 40 wt %, preferably 5-25 wt % and especially 5-15 wt %. The further oily substances are usually comprised in an amount from 0.1 to 40 wt %.

For example, Guerbet alcohols based on fatty alcohols with 6 to 18, preferably 8 to 10 carbon atoms may come into consideration as further oily substances, as well as esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. The following are also suitable: esters of $C_{18}$-$C_{38}$ alkyl hydroxycarboxylic acids with linear or branched $C_6$-$C_{22}$ fatty alcohols, especially dioctyl malates, esters of linear and/or branched fatty acids with polyhydric alcohols (e.g. propylene glycol, dimer diol or trimer triol), triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, e.g. dicaprylyl carbonates (Cetiol® CC), Guerbet carbonates based on fatty alcohols with 6 to 18, preferably 8 to 10 carbon atoms, esters of benzoic acid with linear and/or branched $C_8$-$C_{22}$ alcohols (e.g. Finsolv® TN), linear or branched, symmetric or asymmetric dialkyl ethers with 6 to 22 carbon atoms per alkyl group, e.g. dicaprylyl ether (Cetiol® OE), ring opening products of epoxidized fatty acid esters with polyols and hydrocarbons or mixtures thereof. Esters of 2-propyl heptanol with n-octanoic acid, e.g. commercially available under the trade name Cetiol® SenSoft (Cognis GmbH), are also suitable. Hydrocarbons, such as for example undecane and tridecane, are also suitable. Alkanes, for example the mixtures with the INCI name Coconut/Palm/Palm Kernel Oil Alkanes (trade name Vegelight 1214 from the company Biosynthesis), are also suitable.

It was found, surprisingly, that the compounds according to the invention are suitable in particular for solubilizing oil-soluble crystalline UV-light protection filters.

One aspect of the invention relates to preparations comprising at least one compound according to claim 1 and at least one UV-light protection filter, preferably an oil-soluble UV-light protection filter.

Suitable UV-light protection filters according to the invention are room-temperature liquid or crystalline organic substances (light protection filters) that are able to absorb ultraviolet radiation and reemit the absorbed energy in the form of longer-wave radiation, e.g. heat. UV filters can be oil-soluble or water-soluble. The following may be mentioned for example as typical oil-soluble UV-B filters or broad-spectrum UV A/B filters:

- 3-Benzylidene camphor or 3-benzylidene norcamphor (Mexoryl SDS 20) and derivatives thereof, e.g. 3-(4-methylbenzylidene)camphor as described in EP 0693471 B1
- 3-(4'-Trimethylammonium)benzylidene-bornan-2-one-methylsulfate (Mexoryl SO))=
- 3,3'-(1,4-Phenylenedimethine)-bis(7,7-dimethyl-2-oxobicyclo-[2.2.1]heptane-1-methanesulfonic acid) and salts (Mexoryl SX))=
- 3-(4'-Sulfo)-benzylidene-bornan-2-one and salts (Mexoryl SL))=
- Polymers of N-{(2 and 4)-[2-oxoborn-3-ylidene) methyl}benzyl]acrylamide (Mexoryl SW)
- 2-(2H-Benzotriazol-2-yl)-4-methyl-6-(2-methyl-3-(1,3,3, 3-tetramethyl-1-(trimethylsilyloxy)disiloxanyl)propyl) phenol (Mexoryl SL)
- 4-Aminobenzoic acid derivatives, preferably 4-(dimethylamino)benzoic acid-2-ethylhexyl ester, 4-(dimethylamino)benzoic acid-2-octyl ester and 4-(dimethylamino)benzoic acid amyl ester;
- Esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylenes);
- Esters of salicylic acid, preferably salicylic acid-2-ethylhexyl ester, salicylic acid-4-isopropylbenzyl ester, salicylic acid homomethyl ester;
- Derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- Esters of benzalmalonic acid, preferably 4-methoxybenzmalonic acid di-2-ethylhexyl ester;
- Triazine derivatives, e.g. 2,4,6-trianilino-(p-carbo-2'-ethyl-1'-hexyloxy)-1,3,5-triazine and 2,4,6-tris[p-(2-ethylhexyl-oxycarbonyl) anilino]-1,3,5-triazine (Uvinul T 150) as described in EP 0818450 A1 or 4,4'-[(6-[4-((1,1-dimethylethyl)amino-carbonyl)phenyl-amino]-1,3,5-triazine-2,4-diyl)diimino]bis(benzoic acid-2-ethylhexyl ester) (Uvasorb® HEB);
- 2,2-(Methylene-bis(6-(2H-benzotriazol-2-yl)-4-(1,1,3,3-tetramethyl-butyl)phenol) (Tinosorb M);
- 2,4-bis[4-(2-Ethylhexyloxy)-2-hydroxyphenyl]-6-(4-methoxyphenyl)-1,3,5-triazine (Tinosorb S);
- Propane-1,3-diones, e.g. 1-(4-tert-butylphenyl)-3-(4'-methoxyphenyl)propane-1,3-dione;
- Ketotricyclo(5.2.1.0)decane derivatives, as described in EP 0694521 B1;
- Dimethicodiethylbenzalmalonate (Parsol SLX).

The following may be considered as water-soluble UV filters:

- 2-Phenylbenzimidazole-5-sulfonic acid and alkali, alkaline-earth, ammonium, alkylammonium, alkanolammonium and glucammonium salts thereof;
- 2,2(-(1,4-Phenylene)bis(1H-benzimidazole-4,6-disulfonic acid, monosodium salt) (Neo Heliopan AP)
- Sulfonic acid derivatives of benzophenones, preferably 2-hydroxy-4-methoxybenzophenone-5-sulfonic acid and salts thereof;
- Sulfonic acid derivatives of 3-benzylidene camphor, e.g. 4-(2-oxo-3-bornylidenemethyl)-benzene sulfonic acid and 2-methyl-5-(2-oxo-3-bornylidene)sulfonic acid and salts thereof.

In a preferred embodiment of the invention the preparations comprise at least one oil-soluble UV-light protection filter and at least one water-soluble UV-light protection filter.

As typical UV-A filters, consideration may be given in particular to derivatives of benzoyl methane, for example 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)-propane-1,3-dione and enamine compounds, as described in DE 19712033 A1 (BASF) and benzoic acid, 2-[4-(diethylamino)-2-hydroxy-benzoyl]-, Hexyl Ester (Uvinul® A plus).

The UV-A and UV-B filters can of course also be used in mixtures. Particularly favorable combinations consist of the derivatives of benzoyl methane, e.g. 4-tert-butyl-4'-methoxy-dibenzoylmethane (Parsol® 1789) and 2-cyano-3,3-phenyl-cinnamic acid-2-ethyl-hexyl ester (Octocrylenes) in combination with esters of cinnamic acid, preferably 4-methoxycinnamic acid-2-ethylhexyl ester and/or 4-methoxycinnamic acid propyl ester and/or 4-methoxy cinnamic acid isoamyl ester. Advantageously, said combinations are combined with water-soluble filters, e.g. 2-phenylbenzimidazole-5-sulfonic acid and alkali, alkaline-earth, ammonium, alkylammonium, alkanolammonium and glucammonium salts thereof.

Suitable UV-light protection filters are in particular those substances permitted according to Annex VII of the Commission Directive (in the version Commission Directive 2005/9/EC of 28 Jan. 2005 amending Council Directive 76/768/EEC, concerning cosmetic products, for the purposes of adapting Annexes VII thereof to technical progress), to which reference is made here explicitly.

The preparations according to the invention can also comprise insoluble light-protection pigments, namely finely divided metal oxides or salts. Examples of suitable metal oxides are in particular zinc oxide and titanium dioxide and in addition oxides of iron, zirconium, silicon, manganese, aluminum and cerium and mixtures thereof. Silicates (talc), barium sulfate or zinc stearate can be used as salts. The oxides and salts are used in the form of pigments for skin-care and skin-protecting emulsions as well as for decorative cosmetics. The particles should have an average diameter of less than 100 nm, preferably between 5 and 50 nm and especially between 15 and 30 nm. They can have a spherical shape, but particles can also be used that have an ellipsoidal shape or deviate in some other way from spherical. The pigments can also have been surface-treated, i.e. hydrophilized or hydrophobized. Typical examples are coated titanium dioxides, e.g. titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples of are zinc oxides, e.g. Zinc Oxide neutral, Zinc Oxide NDM (Symrise) or Z-Cote® (BASF) or SUN-ZnO-AS and SUNZnO-NAS (Sunjun Chemical Co. Ltd.). As hydrophobic coating agents, consideration may be given in particular to silicones and especially trialkoxyoctyl silanes or simethicones. Preferably so-called micro- or nanopigments are used in sunscreen agents. Micronized zinc oxide is preferably used. Further suitable UV-light protection filters are given in the review of P. Finkel in SÖFW-Journal 122, 8/1996, p. 543-548 and Parf. Kosm. Vol. 80, No. 3/1999, p. 10 to 16.

In addition to the two aforementioned groups of primary light protective substances, it is also possible to use secondary light protective agents of the antioxidant type, which interrupt the photochemical reaction chain that is triggered when UV radiation penetrates the skin. Typical examples of this are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine-sulfoximine, butionine sulfones, penta-, hexa-, heptathionine sulfoximine) at very low compatible dosages (e.g. pmol to mol/kg), in addition (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin-E-acetate), vitamin A and derivatives (vitamin-A-palmitate) and coniferyl benzoate of benzoin resin, rutinic acid and derivatives thereof, α-glycosylrutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and its derivatives (e.g. ZnO, ZnSO$_4$), selenium and its derivatives (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of these stated active substances that are suitable according to the invention.

In a preferred embodiment of the invention the preparations comprise at least one UV-light protection filter selected from the group consisting of 4-methybenzylidene camphor, benzophenone-3, butyl methoxydibenzoylmethane, bis-ethylhexyloxyphenol methoxyphenyl triazine, methylene bis-benzotriazolyl tetramethylbutylphenol, diethylhexyl butamido triazone, ethylhexyl triazone and diethylamino hydroxybenzoyl hexyl benzoate, 3-(4'-trimethylammonium) benzylidene-bornan-2-one-methylsulfate, 3,3'-(1,4-phenylenedimethine)-bis(7,7-dimethyl-2-oxobicyclo-[2.2.1] heptane-1-methanesulfonic acid) and salts thereof, 3-(4'-sulfo)-benzylidene-bornan-2-one and salts thereof, polymer of N-{(2 and 4)-[2-oxoborn-3-ylidene)methyl}benzyl]acrylamide, 2-(2H-benzotriazol-2-yl)-4-methyl-6-(2-methyl-3-(1,3,3,3-tetramethyl-1-(trimethylsilyloxy)disiloxanyl)propyl)phenol, dimethicodiethyl benzalmalonate and mixtures thereof.

These UV-light protection filters are commercially available for example under the following trade names:
NeoHeliopan® MBC (INCI: 4-methybenzylidene camphor; manufacturer: Symrise); NeoHeliopan® BB (INCI: benzophenone-3, manufacturer: Symrise); Parsol® 1789 (INCI: butyl methoxydibenzoylmethane, manufacturer: Hoffmann-La Roche (Givaudan); Tinosorb® S (INCI: bis-ethylhexyloxyphenol methoxyphenyl triazine); Tinosorb® M (INCI: methylene bis-benzotriazolyl tetramethylbutylphenol): manufacturer: Ciba Specialty Chemicals Corporation; Uvasorb® HEB (INCI: diethylhexyl butamido triazone, manufacturer: 3V Inc.), Uvinul® 150 (INCI: ethylhexyl triazone, manufacturer: BASF AG); Uvinul® A plus (INCI: diethylamino hydroxybenzoyl hexyl benzoate: manufacturer: BASF AG; Mexoryl® SO: 3-(4'-trimethylammonium)benzylidene-bornan-2-one-methylsulfate, INCI: camphor benzalkonium methosulfate; Mexoryl® SX: 3,3'-(1,4-phenylenedimethine)-bis(7,7-dimethyl-2-oxobicyclo-[2.2.1] heptane-1-methanesulfonic acid), CTFA: INCI terephthalylidene dicamphor sulfonic acid; Mexory® SL: 3-(4'-sulfo)-benzylidene-bornan-2-one, INCI benzylidene camphor sulfonic acid; Mexoryl® SW: polymer of N-{(2 and 4)-[2-oxoborn-3-ylidene)methyl}benzyl]acrylamide, INCI polyacrylamidomethyl benzylidene camphor; Mexoryl® SL: 2-(2H-benzotriazol-2-yl)-4-methyl-6-(2-methyl-3-(1,3,3,3-tetramethyl-1-(trimethylsilyloxy)disiloxanyl)propyl)phenol, INCI: DROMETRIZOLE TRISILOXANE; Parsol® SLX: dimethicodiethylbenzalmalonate, INCI Polysilicone-15. The preparations according to the invention can comprise the UV-light protection filters in amounts from 0.5 to 30 wt %, preferably 2.5 to 20 wt %, especially preferably 5-15 wt %, relative to the preparation.

Further Ingredients

Suitable thickening agents are for example Aerosil types (hydrophilic silicic acids), carboxymethylcellulose and hydroxyethyl- and hydroxypropylcellulose, polyvinyl alcohol, polyvinyl pyrrolidone and bentonites, e.g. Bentone® Gel VS-5PC (Rheox). A suitable thickener is for example the product available under the trade name Cosmedia® Gel CC with the INCI name dicaprylyl carbonate, stearalkonium hectorite and propylene carbonate. Biogenic active substances include for example tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, e.g. prunus extract, bambara nut extract and vitamin complexes. Deodorizing substances/antiperspirants act against body odors, masking or removing them. Body odors form by the action of skin bacteria on apocrine sweat, wherein degradation products with an unpleasant odor are formed. Accordingly, antibacterial agents, enzyme inhibitors, odor absorbers or odor masking agents, among others, are suitable as deodorizing substances. Insect repellents may include for example N,N-diethyl-m-toluamide, 1,2-pentanediol or 3-(N-n-butyl-N-acetyl-amino)-propionic acid ethyl ester), which is sold under the name Insect Repellent® 3535 by Merck KGaA, and butylacetylaminopropionates. A suitable selftanning agent is dihydroxyacetone or erythrulose. Tyrosine inhibitors, which prevent the formation of melanin and find application in depigmenting agents, include for example arbutin, ferulic acid, kojic acid, cumaric acid and ascorbic acid (vitamin C). Suitable preservatives are for example phenoxyethanol, formaldehyde solution, parabens, pentanediol, chlorphenesin, caprylyl glycol, ethylhexyl glycerols or sorbic acid and the silver complexes known under the designation Surfacine® and the further classes of substances listed in Appendix 6, Part A and B of the Cosmetics Decree. As perfume oils, we may mention mixtures of natural and synthetic fragrances. Natural fragrances are extracts of flowers, stems and leaves, fruit, fruit peel, roots, wood, herbs and grasses, needles and branches, resins and balsams. Furthermore, animal raw materials, for example civet and castoreum and synthetic fragrance compounds such as esters, ethers, aldehydes, ketones, alcohols and hydrocarbons may come into consideration. The following may for example come into consideration as nacreous waxes or nacreous compounds, especially for use in surfactant formulations: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols with 6 to 22 carbon atoms, especially long-chain esters of tartaric acid; fatty substances, for example fatty alcohols, fatty ketones, fatty aldehydes, fatty ethers and fatty carbonates, which have in total at least 24 carbon atoms, especially laurone and distearyl ether; stearyl citrate, cyclodextrin, fatty acids such as stearic acid, hydroxystearic acid or behenic acid, ring opening products of olefin epoxides with 12 to 22 carbon atoms with fatty alcohols with 12 to 22 carbon atoms and/or polyols with 2 to 15 carbon atoms and 2 to 10 hydroxyl groups and mixtures thereof. The overfatting agents used can be substances such as for example lanolin and lecithin and polyethoxylated or acylated lanolin and lecithin derivatives, polyol fatty acid esters, monoglycerides and fatty acid alkanolamides, wherein the latter serve simultaneously as foam stabilizers. A suitable overfatting agent is for example a mixture of cocoglucosides and glyceryl oleate (commercially available as Lamesoft® PO65 from Cognis GmbH).

Suitable fillers are substances which, for example, improve the sensory or cosmetic properties of a preparation and which for example produce or intensify a velvety or silky feel (so-called skin-sensory modifiers). Suitable fillers are starch and starch derivatives (e.g. tapioca starch, aluminum starch octenyl succinates, sodium octenyl succinate, distarch phosphate), pigments, which do not serve mainly as UV filters or colorants (e.g. boron nitride) and/or Aerosil® (CAS No. 7631-86-9), and/or talc, and for example polymethyl methacrylates (e.g. Cosmedia® PMMA V8/V12), silica (e.g. Cosmedia® SILC), stearalkonium hectorite (as comprised in the commercially available product Cosmedia® Gel CC) and HDI/trimethylol hexyllactone crosspolymer (as comprised in the commercially available product Cosmedia® CUSHION).

Metal salts of fatty acids, e.g. magnesium, aluminum and/or zinc stearate or ricinoleate, can be used as stabilizers. For improving the flow behavior, in addition hydrotropes can be used, for example ethanol, isopropyl alcohol, or polyols. Polyols that may come into consideration preferably have 2 to 15 carbon atoms and at least two hydroxyl groups. The polyols can also comprise other functional groups, especially amino groups, or can be modified with nitrogen.

The preparations according to the invention and the compound according to claim 1 are suitable in particular in cosmetic and/or pharmaceutical preparations for wetting or impregnating or coating household and hygiene cloths, which are used for body cleaning and/or for body care.

The following may be mentioned as examples of household and hygiene cloths: tissues, papers, wipes, nonwoven fabric products, sponges, puffs, plasters and bandages, which find application in the area of hygiene and care. They can be moist wipes for baby hygiene and baby care, cleaning wipes, face-cleaning wipes, skin-care wipes, care wipes with active substances against skin aging, wipes with sunscreen formulations and insect repellents and wipes for decorative cosmetics or for after-sun treatment, toilet moist wipes, antiperspirant wipes, diapers, handkerchiefs, wet wipes, hygiene products and selftanning wipes.

Method of Production

Another aspect of the present invention relates to a method of production of compounds of general formula (I), in which alcohols of the general formula $R_1$—OH and/or $R_2$—OH are condensed in the presence of catalysts, wherein $R_1$ and $R_2$ have the meaning given above.

In particular, acid catalysts such as $KHSO_4$, sulfuric acid or alkylsulfuric acid semi-esters and sulfonic acids or esters thereof have proved suitable as catalysts. Heteropolytungstic acids can also be used as catalysts. During etherification, the acid catalysts react with the alcohols partially or completely with ester formation.

Sulfonic acids are especially preferred with the following, $R^5SO_3H(IV)$ in which $R^5$ stands for an alkyl residue with 1 to 4 carbon atoms or an optionally alkyl-substituted aryl residue. Typical examples of suitable sulfonic acids are methanesulfonic acid, ethanesulfonic acid, propanesulfonic acid, butanesulfonic acid, sulfo-oleic acid or p-toluenesulfonic acid, trifluoromethanesulfonic acid, especially methanesulfonic acid, alkylbenzenesulfonic acid and naphthalenesulfonic acid. Moreover, adducts of sodium hydrogen sulfite on olefinic systems, especially on maleic acid, have proved suitable as further sulfonic acids. A typical example of this is sulfosuccinic acid.

The dehydration of the alcohols $R_1$—OH and/or $R_2$—OH can take place in the presence of 0.01 to 10 wt %, preferably 0.01 to 3 wt %, especially 0.01 to 1 wt %—relative to the alcohols—of the sulfonic acids.

For carrying out the method according to the invention, the alcohols $R_1$—OH and/or $R_2$—OH are mixed and brought to the reaction temperature. The reaction is preferably carried out at a temperature from 120 to 260° C., especially preferably 140° C. to 250° C., in particular 180 to 220° C.

The reaction can be carried out under inert gas atmosphere, e.g. under nitrogen atmosphere. The reaction can be carried out at normal pressure or at pressure increased to about 4 bar. Increased pressure is desirable especially when alcohols are used whose boiling point is below the reaction temperature.

Another aspect of the present invention relates to a method of production of compounds of general formula (I), in which an alcohol of general formula $R_1$—OH and/or $R_2$—OH is reacted in the presence of an alkyl halide of general formula $R_1$—X and/or $R_2$—Y, wherein $R_1$ and $R_2$ have the meaning given above and X and Y are selected from the group consisting of chloride, fluoride, bromide and iodide.

The method according to the invention is usually carried out at 20 to 250° C., especially at 25 to 150° C., especially at 40 to 90° C., preferably at 60 to 90° C. The method can be carried out at normal pressure (1 bar) and at increased pressure, i.e. at 2 to 10 bar, preferably at 3 to 5 bar.

The method is usually carried out in the presence of alkaline compounds, for example alkali metal hydroxides, such as sodium hydroxide or potassium hydroxide.

EXAMPLES (1) Production Examples

Production Example 1

Propylheptyl-methyl ether 949.8 g of propylheptanol (6 mol) and 320.0 g of NaOH (50%) (4 mol) were heated to 220° C. on a water separator for 10 hours. 596.4 g of methyl iodide (4 mol) was added to the resultant viscous alcoholate and it was heated to 80° C. for a further 10 h. First the sodium iodide that formed was removed from the product by filtration and then the product was distilled using a packed column. The product is obtained as colorless oil of low viscosity.

Production Example 2

Di(2-propylheptyl)ether 600 g of propylheptanol (3.8 mol), 12 g of trifluoromethanesulfonic acid (50%, 0.04 mol) and 12 g of hypophosphorous acid (0.09 mol) were heated slowly on a dephlegmator to 160° C. and this temperature was maintained for 6 h. After cooling, it was neutralized with 25 g sodium hydroxide solution (50%, 313 mmol) and then the product was distilled on a packed column. The product boils at 120° C. at 0.001 bar and is obtained as colorless oil.

(2) Skin Compatibility

The di(2-propylheptyl)ether obtained according to production example 2 was compared in an occlusive epicutaneous 24 h patch test against the commercially available di-n-octyl ether. For this, 22 test subjects each had 75 μA of the test substances applied on their back (patch test system: Finn Chambers® with occlusive filter containers on Scanpor®), water was used as the blank control, and a 0.5% solution of SDS (sodium dodecyl sulfate) as positive controls. 24 after application the patch was removed, after a further 6 hours the first visual assessment was carried out, further assessments were carried out 24, 48 and 72 hours after the patch was removed.

The assessment was based on a scale from 0 (no reaction) to 4 (strong reaction) in the categories: erythema formation, edema formation, formation of scales (=squamation) and formation of cracks (=fissuration). A so-called total irritation score RSS value was found from the values obtained.

| Test substance | RSS |
|---|---|
| Blank value | 0.14 |
| Positive control | 7.95 |
| Di-n-alkyl ether (Cetiol ® OE) | 7.1 |
| Di(2-propylheptyl)ether according to production example 2 | 3.62 |

As can be seen from the table, the compound according to the invention shows definitely improved skin compatibility and a better feeling on the skin, compared to the prior art.

Dipropylheptyl ether is especially preferred: dipropylheptyl ether has an improved feeling on the skin compared to dibutyloctyl ether. A sensory assessment by trained subjects established easier distributability and greater spreading on the skin. The feeling on the skin is described by the test subjects as "lighter".

Dipropylheptyl ether has improved skin compatibility, compared to diethylhexyl ether. In an in-vivo patch test, the test substances are applied on human skin and left there for 24 hours. Then an assessment is made with respect to possible occurrence of skin reddening or irritation. As comparison, in each case water and a surfactant solution are tested as negative and positive standards.

(3) Cosmetic Preparations

The following cosmetic preparations were prepared both with the ether according to the invention according to production example 1 (propylheptyl-methyl ether) and with the ether according to the invention according to production example 2 (di(2-propylheptyl)ether). All data are given in percentage by weight relative to the total weight of the preparation.

TABLE 1

| | O/W Body Care Emulsions | | | | | | | | | | |
|---|---|---|---|---|---|---|---|---|---|---|---|
| Ingredients | 1 | 2 | 3 | 4 | 5 | 6 | 7 | 8 | 9 | 10 | 11 |
| C—Cream, L—Lotion | C | C | C | L | C | L | L | C | L | C | C |
| Eumulgin ® VL 75 | | | | | | | | 2.0 | | 1.5 | |
| Dehymuls ® PGPH | | 0.6 | | | | | | | | | |
| Generol ® R | | | 0.5 | | | | | | | | |
| Eumulgin ® B2 | | 2.0 | | | | | | | 2.0 | | |
| Tween ® 60 | | | | 0.2 | | | | | | | |
| Cutina ® E 24 | | | | 0.2 | | | | | | | |
| Hostaphat ® KL 340 N | | | | | | | | | 0.5 | | |
| Lanette ® E | | | | | | | | 0.6 | | | |
| Amphisol ® K | | | | 0.2 | | | | | | | |
| Sodium Stearate | | | | | 0.5 | | | | | | |
| Emulgade ® PL 68/50 | 3.0 | | | | | | 2.0 | | | | 1.2 |
| Eumulgin ® SG | 0.2 | | | | | 0.2 | 0.3 | | | | |
| Eumulgin ® Prisma | | 0.2 | | | | | 0.2 | | | 0.2 | 0.5 |
| Inwitor 372 P | | | | | | 3.0 | | | | 3.0 | |
| Tego ® Care CG | 0.7 | | | | | | | | | | |
| Tego ® Care 450 | | | | | 3 | | 1.0 | | | 1.0 | |
| Cutina ® PES | 2.5 | 2 | 3 | | | 2 | | 1.7 | 2.5 | | 1.2 |
| Cutina ® MD | | | 1 | | 3 | 5 | | 2 | | 3 | |
| Lanette ® 14 | | | | | 1 | | | 4 | | | 4 |
| Lanette ® O | 4.5 | | 4 | | 1 | | | | | | 2 |
| Novata ® AB | | | 1 | | | | | | | | 1 |
| Emery ® 1780 | | | | | | 0.5 | 0.5 | | | | |
| Lanolin, water-free, USP | | | | | | | 1.1 | | | | |
| Cosmedia ® DC | | | 1.5 | 2 | | | 1.5 | 2 | | 1.5 | 1.5 |
| Cetiol ® SB 45 | | | | 1.5 | | | | 2 | | | |
| Cegesoft ® C 17 | | | | | | | | | | | 2 |
| Myritol ® PC | | | | | 5 | | | | | | |
| Myritol ® 331 | 2 | 5 | 1 | | | 6 | | 6 | | | |

TABLE 1-continued

O/W Body Care Emulsions

| Ingredients<br>C—Cream, L—Lotion | 1<br>C | 2<br>C | 3<br>C | 4<br>L | 5<br>C | 6<br>L | 7<br>L | 8<br>C | 9<br>L | 10<br>C | 11<br>C |
|---|---|---|---|---|---|---|---|---|---|---|---|
| Finsolv ® TN | | | 2 | | | 2 | | | | | |
| Propylheptyl-methylether or di(2-propylheptyl) ether | 4 | 3 | 4 | 5 | 4 | 4 | 4 | 6 | 8 | 3 | 5 |
| Cetiol ® Sensoft | 2.0 | | | | | 2.0 | | | | 3.0 | |
| Cetiol ® CC | | 3 | | | | | | 4 | | | 5 |
| Cetiol ® OE | | | | 2.0 | | | | | | 4 | |
| Dow Corning DC ® 245 | | | | 2 | 1 | 1 | | | | | |
| Dow Corning DC ® 2502 | | | | | 2 | 1 | | | | | |
| Prisorine ® 3758 | | | | | | 1 | | | | | |
| Silicone Oil Wacker AK ® 350 | 0.5 | 0.5 | 0.5 | | | 1 | | | | | |
| Cetiol ® 868 | | | | | 2 | | 4 | | | | |
| Cetiol ® J 600 | | 2 | | 3 | 3 | 2 | | | | 5 | |
| Ceraphyl ® 45 | | | | | | | 3 | | | | |
| Mineral Oil | | | | | 9 | | | | | | |
| Cetiol ® SN | | | | 5 | | | | | | | |
| Cetiol ® B | | | | | | | | 4 | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond Oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | 1 | | | | | |
| Bisabolol | | | | | | | 0.2 | | | | |
| Tocopherol/Tocopheryl Acetate | | | | | | | 1 | | | | |
| Veegum ® Ultra | | | | | | | | | 1 | | |
| Keltrol ® T | | | | 0.4 | | | | | | 0.5 | |
| Cosmedia ® SP | | 0.3 | | 0.2 | 0.2 | | | | | 0.2 | 0.3 |
| Pemulen ® TR 2 | 0.3 | | | | | | | | 0.3 | | |
| Carbopol ® Ultrez 10 | | | | | | 0.2 | | | | | |
| Rheocare ® C Plus | | | 0.3 | | 0.2 | | | | | | |
| Ultragel ™ 300 | | | | | | | | | | 0.2 | |
| Ethanol | | | | | | | | | | | 10 |
| Butylene glycol | | | | 4 | 3 | | | 2 | 5 | 2 | |
| Glycerin | 2 | | 5 | 5 | | 3 | 3 | 2 | | 4 | 3 |
| Water, Preservatives, NaOH | to 100, q.s., pH 6.5-7.5 | | | | | | | | | | |

TABLE 2

O/W Body Care Emulsions

| Ingredients<br>C—Cream, L—Lotion | 12<br>C | 13<br>C | 14<br>L | 15<br>C | 16<br>L | 17<br>C | 18<br>C | 19<br>L | 20<br>L | 21<br>L | 22<br>C |
|---|---|---|---|---|---|---|---|---|---|---|---|
| Eumulgin ® VL 75 | | | 1 | | | | | | | | 1 |
| Generol ® R | | | | | | 0.3 | | | | | |
| Eumulgin ® B2 | | | | | | | | | | 2 | |
| Tween ® 60 | | | | | 2 | | | | | 1 | |
| Cutina ® E 24 | | | | | 0.5 | | | | | 1 | |
| Lanette ® E | 0.5 | | | | | | | | | | |
| Amphisol ® K | | 0.5 | | | | | | | 0.1 | | |
| Sodium Stearate | | | | | 1 | | | | | | |
| Emulgade ® PL 68/50 | | 3 | | | | 3.0 | | 1 | 2 | | |
| Eumulgin ® SG | | | | | | | 0.5 | | | | 0.5 |
| Eumulgin ® Prisma | | | 0.5 | | | 0.2 | 0.2 | | | | |
| Inwitor 372 P | 3 | 2 | 3 | | 3 | | 1 | 1 | | | |
| Tego ® Care 450 | | | | | 1 | 2.0 | 3.8 | 1 | | | |
| Cutina ® PES | 2 | | 1 | | 2.5 | 2 | | | 1.2 | 1.5 | 3 |
| Cutina ® MD | 3 | 1 | | 4 | | | | | | | |
| Lanette ® 14 | | 2 | | | 1 | | | 2 | | 1 | |
| Lanette ® O | 2 | | | 2 | | 3 | 1 | | 1 | 1 | 6 |
| Novata ® AB | | | | | | | | | 1 | 1 | |
| Emery ® 1780 | | | | | | | | | | | 0.5 |
| Lanolin, water-free, USP | | | | | | 4 | | | | | |
| Cosmedia ® DC | | | 1 | | | 1.5 | | 1 | 1 | | |
| Cetiol ® SB 45 | | | | | | | 2 | | | | |
| Cegesoft ® C 17 | 4 | | | | | | | | | | |
| Myritol ® PC | 6 | | | | | 5 | | | 5 | | |
| Myritol ® 331 | | | 5 | | | | 7 | | | 10 | 3 |
| Finsolv ® TN | | | 5 | | 4 | 5 | | | | | 1 |

TABLE 2-continued

O/W Body Care Emulsions

| Ingredients<br>C—Cream, L—Lotion | 12<br>C | 13<br>C | 14<br>L | 15<br>C | 16<br>L | 17<br>C | 18<br>C | 19<br>L | 20<br>L | 21<br>L | 22<br>C |
|---|---|---|---|---|---|---|---|---|---|---|---|
| Propylheptyl-methylether or di(2-propylheptyl) ether | 5 | 2 | 4 | 6 | 2 | 5 | 4 | 3 | 3 | 8 | 2 |
| Cetiol ® Sensoft | | 2 | | 3 | | | | | | | |
| Cetiol ® CC | | | 4 | | | | | 3 | | | |
| Cetiol ® OE | 2.5 | | | | | 2 | | | 5 | | |
| Dow Corning DC ® 245 | | | | 1 | 3 | | | | | | 2 |
| Dow Corning DC ® 2502 | | 1 | | 1 | | | | | | | 3 |
| Prisorine ® 3758 | 3 | | | | | | | | | | 2 |
| Silicone Oil Wacker AK ® 350 | | | | 1 | | | | | | | 1 |
| Cetiol ® 868 | | 2 | | | | | | | | | |
| Cetiol ® J 600 | | 2 | | 2 | | | | | | | |
| Ceraphyl ® 45 | | | | | | | 3 | | | | |
| Cetiol ® SN | | | 5 | | | | | | | | |
| Cetiol ® B | | | | | | 5 | | 4 | | | 3 |
| Eutanol ® G | | 3 | | 5 | | | | | | | |
| Cetiol ® PGL | | | | | | | | | 5 | 2 | |
| Dry Flo ® Plus | | 1 | | | | | | | | | 1 |
| SFE 839 | 1 | 1 | | | | | | | | | |
| Almond Oil | | | | | | 2 | | | | | |
| Photonyl ® LS | | | | | | 2 | | | | | |
| Panthenol | | | | | | 1 | | | | | |
| Bisabolol | | | | | | 0.2 | | | | | |
| Tocopherol/Tocopheryl Acetate | | | | | | 1 | | | | | |
| Veegum ® Ultra | | | | | | | | 1 | | | |
| Keltrol ® T | | | | | | | | 0.5 | | | |
| Cosmedia ® SP | 0.1 | | 1 | | 0.2 | 0.2 | 0.2 | 0.2 | | | 0.5 |
| Carbopol ® ETD 2001 | | | | 0.3 | | | | | | | |
| Pemulen ® TR 2 | | | | | | 0.3 | | | | | |
| Rheocare ® C Plus | 0.2 | 0.3 | | | | | | | | | |
| Ultragel ™ 300 | | | | 0.4 | | 0.3 | | | 0.4 | | |
| Ethanol | | 5 | | 8 | | | | | | 10 | |
| Butylene glycol | 5 | | | 3 | 3 | | | | 8 | | |
| Glycerin | 2 | 4 | 3 | 3 | | 7 | 5 | 3 | 5 | | |
| Water, Preservatives, NaOH | to 100, q.s., (pH 6.5-7.5) | | | | | | | | | | |

TABLE 3

O/W Body Care Emulsions

| Ingredients<br>C—Cream, L—Lotion, SC = Sprayable Cream | 23<br>SC | 24<br>C | 25<br>C | 26<br>L | 27<br>C |
|---|---|---|---|---|---|
| Dehyquart ® C 4046 | | | 6 | | 3 |
| Cutina ® GMS-SE | | | | | 5.5 |
| Cutina ® FS 45 | | | | | 1.5 |
| Eumulgin ® B2 | | | 1 | | |
| Eumulgin ® SG | | | | 0.2 | |
| Eumulgin ® Prisma | | | 0.2 | | |
| Inwitor 372 P | | | | 2 | |
| Cutina ® PES | | 3 | 2 | 2 | 2 |
| Cutina ® MD | | | 1.5 | | |
| Cosmedia ® DC | | | | 0.5 | |
| Cegesoft ® PS 6 | | | | 4.5 | |
| Cegesoft ® SH | | | 7 | 3 | |
| Myritol ® 331 | | | | 5 | 4.5 |
| Propylheptyl-methylether or di(2-propylheptyl) ether | 4 | 5 | 4 | 3 | 4 |
| Cetiol ® Sensoft | | | 2 | | |
| Cetiol ® CC | | | | | 3 |
| Cetiol ® OE | | 1 | | | |
| Silicone Oil Wacker AK ® 350 | | | | | 0.5 |
| Paraffin Liquid | | | | | 2 |
| Isopropyl Palmitate | | | | 2 | |
| Cetiol ® 868 | | | 2 | 4 | |
| Cetiol ® SN | 4 | | | | 3 |
| Eutanol ® G | | | | | 3 |
| Almond Oil | | 7 | | | |
| Panthenol | 1 | 0.2 | 1 | | |
| Bisabolol | | | 1 | | |
| Tocopherol/Tocopheryl Acetate | | | 0.2 | | |
| Keltrol ® T | | | 1 | | |
| Ultragel ™ 300 | 0.1 | | | 0.45 | |
| Cosmedia ® SP | | 1 | 0.7 | | |
| Glycerin | 2 | 5 | 5 | 5 | |
| Water, Preservatives, NaOH | to 100, q.s. | | | | |

TABLE 4

W/O Body Care Emulsions

| Ingredients (INCI)<br>L = Lotion, C = Cream | 1<br>C | 2<br>L | 3<br>C | 4<br>L | 5<br>C | 6<br>L | 7<br>L | 8<br>L | 9<br>C | 10<br>C | 11<br>C |
|---|---|---|---|---|---|---|---|---|---|---|---|
| Dehymuls ® PGPH | 1 | 2 | 1 | 2 | 3 | 1 | | 1 | 2 | | 1 |
| Monomuls ® 90-O18 | 2 | | | | | | | | 2 | | 2 |
| Lameform ® TGI | 4 | 1 | | | 3 | | | 1 | 4 | 3 | |
| Abil ® EM 90 | | | | | | | 4 | | 1 | | |

TABLE 4-continued

W/O Body Care Emulsions

| Ingredients (INCI) L = Lotion, C = Cream | 1 C | 2 L | 3 C | 4 L | 5 C | 6 L | 7 L | 8 L | 9 C | 10 C | 11 C |
|---|---|---|---|---|---|---|---|---|---|---|---|
| Isolan GPS | | | 2 | | 2 | | | | | 1 | |
| Isolan ® PDI | | | | | | 4 | | | | | 1 |
| Glucate ® DO | | | | 3 | | | | | | | |
| Arlacel ® 83 | | | | 4 | | | | | | | |
| Dehymuls ® LE | | 1 | 1 | | 2 | | | | | 1 | 1 |
| Dehymuls ® HRE 7 | | | | | | | | | 4 | 1 | |
| Zinc Stearate | 2 | 1 | | 1 | 1 | | | | 1 | 1 | 1 |
| Microcrystalline Wax | | | 5 | | | 2 | | | | | 5 |
| Beeswax | 4 | | | 1 | | | | | 1 | 4 | 7 |
| Tego Care ® CG | | | | | 1 | | | | | | 0.5 |
| Prisorine ® 3505 | | | 1 | 1 | | 1 | 1 | | | | 1 |
| SFE ® 839 | | | | | | | 3 | | | | |
| Emery ® 1780 | 1 | | | | | | | | | | 1 |
| Anhydrous Lanolin USP | | | 5 | | | | | | | 4 | |
| Propylheptyl-methylether or di(2-propylheptyl) ether | 3 | 4 | 2 | 6 | 6 | 2 | 2 | 6 | 3 | 8 | 1 |
| Cegesoft ® C 17 | | | 3 | | | | | | | 1 | |
| Myritol ® PC | | | | | | 2 | | 4 | | | |
| Myritol ® 331 | 6 | | | | 2 | 6 | 2 | | | 8 | |
| Finsolv ® TN | | | | 5 | | 2 | 5 | | | | |
| Cetiol ® A | | 6 | | | 4 | | | | | | |
| Cetiol ® Sensoft | | | | 6 | 4 | | | | | 4 | |
| Cetiol ® CC | | 8 | | | 2 | 2 | 2 | | | 5 | |
| Cetiol ® SN | | 5 | | | | | | 3 | | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | 1 | | 2 | | | | | | |
| Prisorine ® 3758 | | | | | 3 | | | | | | |
| Silicon Oil Wacker AK ® 350 | | | | 4 | | | | 3 | | | |
| Cetiol ® 868 | | | | | | | | | | 2 | 7 |
| Cetiol ® J 600 | | | 4 | | 2 | | | | | 6 | |
| Ceraphyl ® 45 | | | | 2 | | | | 2 | | 6 | |
| Mineral oil | | | | 4 | | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | 4 | | | | 9 | | |
| Almond Oil | | | | 1 | | 5 | | | | | |
| Insect Repellent ® 3535 | 2 | | | | | | | | | | |
| Unirep ® U-18 | | | | 3 | | | | 5 | | | |
| Photonyl ® LS | 2 | 2 | | | | | | | | | |
| Panthenol | | | | | | 1.0 | | | | | |
| Bisabolol | | | | | | 0.2 | | | | | |
| Copherol ® 1250 C | | | | | | 1 | | | | | |
| MgSO₄ × 7 H₂O | | | | | | 1 | | | | | |
| Bentone ® 38 | | | | | 1 | | | | | | |
| Propylene Carbonate | | | | | 0.5 | | | | | | |
| Ethanol | | | | | | | | | | 8 | |
| Butylene Glycol | | | 2 | 6 | | | 2 | 5 | | 2 | |
| Glycerin | 5 | 3 | 3 | | 5 | 3 | 2 | | 10 | 4 | |
| Water, Preservative | | | | | to 100, q.s. | | | | | | |

TABLE 5

O/W Sun Care Emulsions

| Ingredients C—Cream, L—Lotion | 1 L | 2 C | 3 S | 4 L | 5 C | 6 L | 7 L | 8 C | 9 L | 10 C | 11 L |
|---|---|---|---|---|---|---|---|---|---|---|---|
| Eumulgin ® VL 75 | 2.0 | | | | | | | 2 | | | 2 |
| Eumulgin ® B2 | | | | 0.5 | | | | | | | |
| Tween ® 60 | | | | 0.2 | | | | | | | |
| Myrj ® 51 | | | | 0.5 | | | | | | | |
| Cutina ® E 24 | | | | 0.1 | | | | | | | |
| Hostaphat ® KL 340 N | | | | | | | | | 1.6 | | |
| Lanette ® E | | | 0.3 | | | | | | | | |
| Amphisol ® K | | | | | | | | | | 1 | |
| Sodium Stearate | | | | | | | 1 | | | | |
| Emulgade ® PL 68/50 | | 2 | 1 | | | 2 | 2 | | | 2 | |
| Imwitor 372 P | | 2 | | | | | 1 | 2 | | | |

TABLE 5-continued

O/W Sun Care Emulsions

| Ingredients<br>C—Cream, L—Lotion | 1<br>L | 2<br>C | 3<br>S | 4<br>L | 5<br>C | 6<br>L | 7<br>L | 8<br>C | 9<br>L | 10<br>C | 11<br>L |
|---|---|---|---|---|---|---|---|---|---|---|---|
| Eumulgin ® SG | | 0.5 | | | | 0.1 | | 0.2 | | | |
| Eumulgin ® Prisma | 0.1 | | | | 0.75 | | | | | | |
| Tego ® Care 450 | | | | | | 2 | | | | 1 | 2.5 |
| Cutina ® PES | 2 | | 2.5 | 1 | 2.5 | | 2.5 | | 2.5 | 1.7 | 1.5 |
| Cutina ® MD | 2 | | 1 | 2 | | | 2 | | | 6 | |
| Lanette ® 14 | 1 | | | 1 | | | | 2 | | | 2 |
| Lanette ® O | 1 | 6 | | | 5 | 2 | | 2 | | | |
| Cosmedia ® DC | 1 | 1.5 | | 1 | 1 | | 2 | 2 | | | 2 |
| Antaron ® V 216 | | | 2 | | | 1.5 | | | 1 | 1 | |
| Emery 1780 | | | | | | 0.5 | 0.5 | | | | |
| Lanolin, water-free USP | | | | | | | | 5 | | | |
| Myritol ® PC | | | | | 5 | | | | | | |
| Myritol ® 331 | | | 8 | | | 6 | | 10 | | 2 | |
| Finsolv ® TN | | | 1 | | | | | 1 | | | |
| Propylheptyl-methylether or di(2-propylheptyl) ether | 5 | 2 | 3 | 5 | 3 | 4 | 3 | 2 | 5 | 2 | 5 |
| Cetiol ® Sensoft | | 2.5 | | | 2 | | | | 3 | | |
| Cetiol ® CC | | | 2 | | | | 1 | | | | |
| Cetiol ® OE | | | 3 | | | | | | 2 | 3 | |
| Dow Corning DC ® 244 | 4 | | 1 | | | | | 2 | | | 2 |
| Dow Corning DC ® 2502 | | 1 | | | 2 | | | | | | |
| Squatol ® S | | | | | | | 4 | | | | |
| Silicone Oil Wacker AK ® 350 | | 2 | | | | | | | | | |
| Cetiol ® 868 | | | | | | 2 | | 4 | | | 2 |
| Cetiol ® J 600 | | | | | | 3 | 2 | | | 5 | |
| Mineral Oil | | | | 4 | | | | | | | |
| Cetiol ® B | | | 1 | | | | | | | 2 | |
| Eutanol ® G | | | | 2 | | | | | 4 | | |
| Eutanol ® G 16 | 4 | | | | | 4 | | | | | |
| Cetiol ® PGL | | 5 | | | | | | | | 5 | |
| Almond Oil | | | 2 | | | | | 1 | | | |
| Photonyl ® LS | | | | 2 | | | | | | 2 | |
| Panthenol | | | | | | 1 | | | | | |
| Bisabolol | | | | | | 0.2 | | | | | |
| Tocopherol/Tocopheryl Acetate | | | | | | 1 | | | | | |
| Photonyl ® LS | | | | | | | | | | | |
| Neo Heliopan ® AP (Na-salt) | | 1 | | | | | | | 1 | | |
| Neo Heliopan ® Hydro (Na-salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | | 10 | 7 |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® A Plus | | | | 2 | 1 | | | | | | |
| Uvinul ® T 150 | 2 | | | | 2.5 | | | 1 | | | |
| Tinosorb ® M | | | 3 | | | | 2 | | | | 3 |
| Tinosorb ® S | | | 1 | | | | 1.5 | | | | |
| Uvasorb ® HEB | | 1 | | | 1 | | | | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | 0.1 | 0.5 | | | 0.5 | | 0.2 | 0.2 | | 0.2 | 0.2 |
| Ultragel ™ 300 | | | | 0.2 | | 0.2 | | | 0.1 | | |
| Rheocare ® C plus | | | | | | | | | | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservatives, NaOH, Water | | | | | q.s. to 100 | | | | | | |

TABLE 6

O/W Sun Care Emulsions

| Ingredients<br>C—Cream, L—Lotion | 12<br>L | 13<br>C | 14<br>L | 15<br>C | 16<br>L | 17<br>C | 18<br>S | 19<br>C | 20<br>C | 21<br>L | 22<br>L |
|---|---|---|---|---|---|---|---|---|---|---|---|
| Eumulgin ® VL 75 | | | 4 | | 1.8 | | | | | | |
| Eumulgin ® B2 | | | | | | | | | 0.2 | | |
| Tween ® 60 | | | | | | | | | 0.3 | | |

TABLE 6-continued

| | O/W Sun Care Emulsions | | | | | | | | | | |
|---|---|---|---|---|---|---|---|---|---|---|---|
| Ingredients | 12 | 13 | 14 | 15 | 16 | 17 | 18 | 19 | 20 | 21 | 22 |
| C—Cream, L—Lotion | L | C | L | C | L | C | S | C | C | L | L |
| Cutina ® E 24 | | | | | | | | | | 0.5 | |
| Hostaphat ® KL 340 N | | | | | | | | | | | 0.5 |
| Imwitor 372 P | 2 | | | 2 | | | 2 | | 2.0 | | |
| Eumulgin ® SG | | | | 0.1 | | 0.2 | | | | | |
| Eumulgin ® Prisma | | 0.3 | 0.2 | | | | | | | | |
| Lanette ® E | | | | | | | 0.1 | | 0.5 | | |
| Amphisol ® K | 0.5 | | | | | | | 1 | | | |
| Sodium Stearate | | | | | 1 | | | | | | |
| Emulgade ® PL 68/50 | | 1.5 | | 2 | | 3 | | 2 | | | |
| Tego ® Care 450 | 1 | | | | | 2 | | 2 | 0.8 | | |
| Cutina ® PES | 2 | 2 | 2.5 | 1.5 | 2 | 2 | 2.5 | 3 | | 1.5 | 1.5 |
| Cutina ® MD | 1 | | | 4 | 1 | 3 | | | 5 | | 1 |
| Lanette ® 14 | | 2 | | | | | | | | 1 | |
| Lanette ® O | | 2 | | 2 | | | | 2 | 1 | 1 | |
| Allianz ® OPT | 1 | | | 1 | 1 | | 1.5 | 2 | | | 2 |
| Cosmedia ® DC | | 1.5 | 2 | | 1 | | 1.5 | 2 | | 1.5 | 1.5 |
| Emery ® 1780 | | | | | 1 | 1 | | | | | |
| Lanolin, water-free, USP | | | | | | | 1 | 1 | | | |
| Myritol ® PC | | | | | | | | | 3 | | |
| Myritol ® 331 | 12 | | 12 | | | 8 | 8 | | | 5 | 3 |
| Finsolv ® TN | | | | | 3 | | | | 3 | | |
| Propylheptyl-methylether or | 4 | 2 | 3 | 5 | 3 | 2 | 4 | 3 | 2 | 5 | 3 |
| di(2-propylheptyl) ether | | | | | | | | | | | |
| Cetiol ® Sensoft | | | 3 | | | 5 | | | | | 2 |
| Cetiol ® CC | 2 | | | | | | 1 | | | | |
| Cetiol ® OE | | | | | 2 | | | | | | 2 |
| Dow Corning DC ® 244 | | | | | 1 | | | | | | |
| Dow Corning DC ® 2502 | | 1 | | | | | | 3 | | | |
| Ceraphyl ® 45 | | | | | | | | | | 2 | 2 |
| Silicone oil Wacker AK ® 350 | | | | | 1 | | | | | | |
| Cetiol ® 868 | | 2 | | | | | | | | | |
| Cetiol ® J 600 | | 2 | | | | | | | | | |
| Mineral Oil | | | | 5 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopheryl Acetate | | | | | | 1 | | | | | |
| Neo Heliopan ® Hydro (Na-salt) | | | | | | | | | | 3 | |
| Eusolex ® OCR | 6 | | 9 | | 5 | 7 | 9 | | 4 | | 7 |
| Neo Heliopan ® AP (Na-salt) | | | | 0.5 | 1 | | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® A PLUS | | | | | 1 | | 2 | | | | |
| Uvinul ® T 150 | 1 | | | | | | | | 1.3 | 1 | 1 |
| Tinosorb ® M | | | 6.5 | | | | | | 4 | | |
| Tinosorb ® S | | | 1 | | 2 | | | | | | |
| Uvasorb ® HEB | 1 | | | | | | | | | | 2 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | 2 | | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | | | | 0.1 | | | | |
| Pemulen ® TR 2 | | 0.3 | | 0.3 | | | | 0.2 | | | |
| Ultragel ™ 300 | | | | | | | | | | 0.2 | 0.3 |
| Rheocare ® C Plus | | | | 0.3 | | | 0.1 | | | | |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/Preservatives/NaOH | | | | | to 100/q.s./q.s | | | | | | |

TABLE 7

W/O Sun Care Emulsions

| Ingredients<br>C—Cream, L—Lotion | 23<br>C | 24<br>L | 25<br>C | 26<br>L | 27<br>C | 28<br>L | 29<br>L | 30<br>L | 31<br>L | 32<br>C | 34<br>C |
|---|---|---|---|---|---|---|---|---|---|---|---|
| Dehymuls ® PGPH | 4 | 3 | 1 | 3 | 2 | 1 | 1 | 1 | | | |
| Monomuls ® 90-018 | | 1 | 2 | | | | | | 2 | 4 | |
| Lameform ® TGI | 2 | | | | 3 | | | | | 1 | 3 |
| Abil ® EM 90 | 2 | | | | | | 4 | | 1 | | 1 |
| Isolan GPS | | | 4 | | 3 | | | 2 | | | |
| Isolan ® PDI | | | | | | 4 | | 2 | | | |
| Zinc Stearate | 1 | | | 1 | 1 | | | 1 | | 1 | |
| Beeswax | 1 | | 5 | 1 | 3 | | | 2 | | 7 | 5 |
| Tego ® Care CG | | | | | 1 | | | | | | 0.5 |
| Cutina ® PES | | | 2 | | | 1 | 1 | | | | |
| Prisorine ® 3505 | | | 1 | | | 1 | 1 | | | | 1 |
| Cosmedia ® DC | 3 | 4 | 2 | 1 | 1 | 2 | 2 | 2 | 3 | 1 | 1 |
| Myritol ® 331 | 2 | | | | 3 | 3 | | | | | 8 |
| Finsolv ® TN | | | | 2 | | | | | | | |
| Propylheptyl-methylether or di(2-propylheptyl) ether | 5 | 4 | 2 | 3 | 4 | 3 | 5 | 5 | 4 | 4 | 5 |
| Cetiol ® Sensoft | | | | 3 | | | 5 | | | 3 | |
| Cetiol ® CC | 5 | | | | | 2 | | | 2 | 3 | |
| Tegosoft ® DEC | | | 4 | | 2 | | | | | | |
| Cetiol ® OE | | | | | 4 | | 5 | | 2 | | |
| Dow Corning ® DC 244 | | | 3 | | | | 2 | | 4 | | |
| Dow Corning ® DC 2502 | 1 | | 1 | | 2 | 1 | | | | | 1 |
| Silicone oil Wacker AK 350 | | 1 | | 4 | | | | 3 | | | |
| Cetiol ® PGL | | 3 | | | | 4 | | 4 | | | |
| Copherol ® F 1300 | | | | | | 1 | | | | | |
| MgSO$_4$ * 7H$_2$O | | | | | | 1 | | | | | |
| Neo Heliopan ® Hydro (Na-salt) | 2 | | 2.2 | | 3 | 3 | | | 1 | | 2 |
| Neo Heliopan ® 303 | | 5 | | | | | | | 4 | | 4 |
| Uvasorb ® HEB | 1 | | | 1 | 1 | | | | | | 2 |
| Neo Heliopan ® MBC | 2 | | | | | 2 | 2 | 2 | | | |
| Uvinul ® A Plus | | | | | 2 | | | | 3 | 3 | |
| Neo Heliopan ® AP (Na-salt) | | 2 | 2 | | 1 | | | | 1 | | 6 |
| Neo Heliopan ® AV | 3 | | 4 | 6 | 4 | 7.5 | 4 | 5 | | | 1 |
| Uvinul ® T 150 | 1 | 1 | | | 2.5 | | | 1 | | | |
| Parsol ® 1789 | 2 | 1 | | | | | 2 | | 2 | 2 | |
| Zinc oxide NDM | | | | | | 10 | | 3 | | | 4 |
| Tinosorb ® M | | 3 | | 3 | | | | 2 | | 2 | |
| Tinosorb ® S | | 3 | | 3 | | | | 2 | | 2 | |
| Eusolex ® T Aqua | | | 8 | | | | | 5 | | | |
| Eusolex ® T 2000 | | | | | 5 | | 3 | 3 | | | 4 |
| Ethanol | | | | | | | | | | 8 | |
| Glycerin | 5 | 3 | 3 | 3 | 5 | 3 | 2 | 3 | 10 | 4 | 3 |
| Water, Preservatives | | | | | to 100, q.s. | | | | | | |

TABLE 8

W/O Sun Care Emulsions

| Ingredients | 12 | 13 | 14 | 15 | 16 | 17 |
|---|---|---|---|---|---|---|
| Dehymuls ® PGPH | 1 | 1 | | | 1 | 1 |
| Dehymuls ® LE | 1 | 2 | 1 | 1 | 1 | 1 |
| Abil ® EM 90 | | | | 4 | | |
| Isolan GPS | 3 | | | 1 | 1 | |
| Isolan ® PDI | | | | 4 | | 2 |
| Zinc Stearate | | | 1 | | | 1 |
| Beeswax | | | 1 | | | 5 |
| Cutina ® PES | | | 1 | | 1 | |
| Prisorine ® 3505 | | | | 1 | 1 | |
| Cosmedia ® DC | 4 | 1 | | 2 | 2 | 3 |
| Myritol ® 331 | | | | 3 | | |
| Finsolv ® TN | | 2 | | | | |
| Propylheptyl-methylether or di(2-propylheptyl) ether | 4 | 3 | 3 | 5 | 5 | 4 |
| Cetiol ® CC | | | | 2 | | 2 |
| Cetiol ® Sensoft | | 2 | | 2 | | 4 |
| Tegosoft ® DEC | 4 | 3 | | | 5 | |
| Cetiol ® OE | 2 | | | | 5 | |
| Dow Corning ® DC 244 | | | | | 2 | 4 |
| Dow Corning ® DC 2502 | | | | 1 | | |
| Silicone oil Wacker AK 350 | 1 | 4 | | | 3 | |
| Cetiol ® PGL | 3 | | 4 | | | 4 |
| Copherol ® F 1300 | | | | 1 | | |
| MgSO$_4$ * 7H$_2$O | | | | 1 | | |
| Neo Heliopan ® Hydro (Na-salt) | | | 3 | | | 1 |
| Neo Heliopan ® 303 | 5 | | | | | 4 |
| Uvasorb ® HEB | | | 1 | | | |
| Neo Heliopan ® MBC | | | | 2 | 2 | 2 |
| Uvinul ® A Plus | | | | | | 3 |
| Neo Heliopan ® AP (Na-salt) | 2 | | | | | 1 |
| Neo Heliopan ® AV | | | 6 | 7.5 | 4 | 5 |
| Uvinul ® T 150 | 1 | | | | | 1 |
| Parsol ® 1789 | 1 | | | 2 | | 2 |
| Zinc oxide NDM | | | 10 | | 3 | |
| Tinosorb ® M | 3 | 3 | | | | 2 |
| Tinosorb ® S | 3 | 3 | | | | 2 |
| Eusolex ® T Aqua | | | | | | 5 |
| Eusolex ® T 2000 | | | | | 3 | 3 |
| Glycerin | 3 | 3 | 3 | 2 | 3 | 10 |
| Water, Preservatives | | | to 100, q.s. | | | |

TABLE 9

Decorative Cosmetics - O/W Foundations

| Ingredients | 1 | 2 | 3 | 4 | 5 | 6 | 7 | 8 |
|---|---|---|---|---|---|---|---|---|
| Cutina ® GMS-SE | 5.5 | | | | | | | 3.0 |
| Emulgade ® PL 68/50 | | 5.0 | | | 2.0 | | | |
| Eumulgin ® VL 75 | | | 3.0 | | | 5.0 | | |
| Tego Care ® 450 | | | | | | 2.0 | 2.0 | |
| Codesta ® F-50 | | | | | 6.0 | | | |
| Amphisol ® K | | | | 2.0 | | | | |
| Lanette ® E | | 0.25 | | | | | | |
| Eumulgin ® SG | | | | | 1.0 | | 1 | |
| Eumulgin ® Prisma | | | | | 1.0 | | | 0.75 |
| Imwitor 372 P | | 2 | | | | | 1 | |
| Cutina ® FS 45 | 1.5 | | | | | | | |
| Eumulgin ® B 2 | | | 2.0 | | | | | |
| Cutina ® PES | 2.0 | 1.0 | 2.0 | 4.0 | 2.0 | 1.0 | 2.5 | 2.0 |
| Lanette ® O | | | 2.0 | | | | | 1.0 |
| Cutina ® MD | | 0.5 | 3.0 | 3.0 | | | | |
| Cetiol ® LC | 4.0 | | | | | | | |
| Cosmedia ® DC | 0.5 | | | 1.0 | | | | 1.0 |
| Propylheptyl-methylether or di(2-propylheptyl) ether | 4.0 | 5.0 | 4.0 | 2.0 | 7.0 | 5.0 | 10.0 | 4.0 |
| Cetiol ® Sensoft | 2.0 | | | | 3.0 | | | 2.0 |
| Tegosoft ® DEC | | 5.0 | | 2.0 | | 2.0 | | 2.0 |
| Cetiol ® CC | | | 2.0 | | 2.0 | | | |
| Dow Corning ® 245 | | 2.0 | | 2.0 | | | | |
| Eutanol ® G 16 | 4.0 | | | | | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | | 1.0 | 1.0 |
| Tinosorb ® M | | | 2.0 | | | | | 2.0 |
| Tinosorb ® S | | | | 3.0 | | | | 2.0 |
| Neo Heliopan ® AV | | | | 2.0 | | | 2.0 | |
| Heo Heliopan ® AP | | | | 1.0 | | | 1.0 | |
| Uvinul ® A Plus | | | 1 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Cosmedia ® SP | | | 0.3 | | 0.2 | | | |
| Water, de-ionized, Preservative | | | | to 100 | | | | |

TABLE 10

Decorative Cosmetics - W/O Foundations

| Ingredients | 1 | 2 | 3 | 4 | 5 | 6 | 7 | 8 |
|---|---|---|---|---|---|---|---|---|
| Dehymuls ® PGPH | 5.5 | | 4.0 | | | | | 3.0 |
| Lameform ® TGI | | 5.0 | | | 2.0 | | | |
| Abil ® EM 90 | | | | 3.0 | | 5.0 | | |
| Isolan ® GI 34 | | | | | | 2.0 | 2.0 | |
| Isolan ® PDI | | | | 1.0 | 6.0 | | | |
| Isolan ® GPS | 1.0 | 2.0 | | 1.0 | | | | |
| Admul ® WOL 1403 | | | | | 2.0 | | | |
| Dehymuls ® HRE 7 | | 1.0 | | | | 1.0 | 1.0 | |
| Monomuls ® 90-018 | 1.5 | | | | | | | 2.0 |
| Cutina ® PES | 2.0 | 1.0 | 2.0 | 4.0 | 2.0 | 1.0 | 2.5 | 2.0 |
| Cera Bellina | | | 2.0 | | | | | 2.0 |
| Beeswax | | | 2.0 | | | 2.0 | | 1.0 |
| Microcrystalline Wax | | 1.5 | 3.0 | 3.0 | | | | |
| Cetiol ® LC | 4.0 | 5.0 | | | | | | |
| Cosmedia ® DC | 1.0 | | | | 0.5 | | 1.0 | |
| Propylheptyl-methylether or di(2-propylheptyl) ether | 4.0 | 2.0 | 2.0 | 4.0 | 5.0 | 5.0 | 5.0 | 4.0 |
| Cetiol ® Sensoft | | | 2.0 | | | 2.0 | | 5.0 |
| Tegosoft ® DEC | | | 3.0 | | | | 2.0 | |
| Cetiol ® CC | | | | | 2.0 | | | 2.0 |
| Dow Corning ® 245 | | | | 2.0 | | 2.0 | | 2.0 |

TABLE 10-continued

Decorative Cosmetics - W/O Foundations

| Ingredients | 1 | 2 | 3 | 4 | 5 | 6 | 7 | 8 |
|---|---|---|---|---|---|---|---|---|
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | | 2.0 | | | | | 1.0 | 1.0 |
| Tinosorb ® M | | | 2.0 | | | | | 2.0 |
| Tinosorb S | | | | 3.0 | | | | 2.0 |
| Neo Heliopan ® AV | | | | | 2.0 | | 2.0 | |
| Heo Heliopan ® AP | | | | | 1.0 | | 1.0 | |
| Uvinul ® A plus | | | 1.0 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | 3.5 | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Water, de-ionized, | | | | to 100 | | | | |
| Preservative | | | | | | | | |

TABLE 11

Decorative Cosmetics - Lipsticks

| Ingredients | 1 | 2 | 3 | 4 |
|---|---|---|---|---|
| Cutina ® LM conc | | | 10.0 | 36.0 |
| Candelilla Wax | 9.39 | 5.0 | 10.0 | |
| Carnauba wax | 2.85 | 7.0 | 5.0 | |
| Beeswax | 1.86 | 5.0 | 4.0 | |
| Cutina ® PES | 3.2 | 5.0 | 6.4 | 4.5 |
| Cetiol ® MM | | | 5.0 | |
| Cosmedia ® DC | 5.0 | 4.0 | 2.0 | 6.0 |
| Propylheptyl-methylether or di(2-propylheptyl) ether | 7.0 | 6.0 | 3.0 | 5.0 |
| Cetiol ® Sensoft | 2.0 | | 4.5 | |
| Tegosoft ® DEC | 3.0 | 3.0 | 3.0 | 5.0 |
| Eutanol ® G | 10.97 | 12.0 | 12.0 | |
| Fitoderm ® | | | 4.0 | |
| Monomuls ® 90L 12 | | 3.0 | | |
| Dehymuls ® PGPH | | 4.0 | | |
| Castor Oil | 11.0 | 15.5 | 14.5 | 30.0 |
| Copherol ® F 1300 | 1.0 | 1.0 | 1.0 | 1.0 |
| Cosmetic white C47056 | 5.0 | 2.0 | 5.0 | |
| FDC Yellow 6 Al Lake C705270 | 7.0 | 7.0 | 8.0 | |
| DC Red 7 Ca Lake C 19003 | 6.0 | 4.5 | 1.1 | 2.9 |
| Irodin 100 Silverpearl | | | | 9.6 |
| Hydagen ® CMF | | 10.0 | | |
| Irwinol ® LS 9319 | 1.0 | | 3.0 | |
| Mineral Oil | 12.8 | | | |
| Petrolatum | 6.84 | 3.0 | | |
| Ceresin | 2.75 | | | |
| Microcrystalline Wax | 2.45 | | | |
| Colophane Claire type Y | 1.89 | | | |

TABLE 12

| Ingredients (INCI) | 1 | 2 | 3 | 4 | 5 | 6 | 7 |
|---|---|---|---|---|---|---|---|
| AP/Deo Concepts | | | | | | | |
| Glyceryl Stearate, Ceteareth-20, Ceteareth-12, Cetearyl Alcohol, Cetyl Palmitate (Emulgade ® SE) | 6 | | | 4.5 | | 6 | |
| Ceteareth-20 (Eumulgin ® B2) | | | | 1 | | | |
| Glyceryl Stearate Citrate (Imwitor 372 P) | | 4.0 | | | | | |
| Polyglyceryl-3 Diisostearate (Lameform ® TGI) | | | 3 | | | | |
| Cocoglycerides (Novata ® AB) | | | | | | | 4 |
| Stearyl alcohol (Lanette ® 18) | | | | | 10 | | |
| Hydrogenated Castor Oil (Cutina ® HR) | | | | | 3.7 | | 6.5 |
| Polyglyceryl-2 Dipolyhydroxystearate (Dehymuls ® PGPH) | | | 1 | | | | |
| Sodium Stearoyl Glutamate (Eumulgin ® SG) | | 0.2 | | | | | |
| Disodium Cetearyl Sulfosuccinate (Eumulgin ® Prisma) | 0.3 | | | | | | |
| Sodium Cetearyl Sulfate (Lanette ® E) | | | | | | 0.3 | |
| Pentaerythrityl Distearate (Cutina ® PES) | 5 | 1 | 2 | 1 | 4.7 | 5 | 4 |
| Behenyl Alcohol (Lanette ® 22) | 2 | 1 | | | | 4 | |
| Propylheptyl-methylether or di(2-propylheptyl) ether | 4 | 4 | 5 | 3 | 4 | 3 | 5 |
| Propylheptyl Caprylate (Cetiol ® Sensoft) | | 2 | | | 20 | | 10 |
| Dicaprylyl Carbonate (Cetiol ® CC) | | | 2 | | | | |
| Dicaprylyl Ether (Cetiol ® OE) | 2 | | | 2 | 5 | 3 | 4 |
| Cocoglycerides (Myritol ® 331) | | | | | | | |
| Diethylhexylcyclohexane (Cetiol ® S) | | | | 5 | 14.7 | | 25 |
| Cyclopentasiloxane | 3 | | 5 | | 14 | 3 | 14 |
| Cyclopentasiloxane and Dimethicone/Vinyldimethicone Crosspolymer SFE 839 (GE Bayer) | | | 3 | | | | |
| Dimethicone AK 350 | 1 | 2 | | | | | |
| Hydrogenated Dimer Dilinoleyl/Dimethylcarbonate Copolymer (Cosmedia ® DC) | 0.5 | | 1 | 1.5 | 1 | 2 | 1 |
| Triethyl Citrate (Hydagen ® C.A.T) | | | | 2 | | | |
| Tocopheryl Acetate | | | | | 1 | | |
| Aluminum Zirconium Tetrachlorohydrex GLY (Rezal 36) | 30 | | 40 | | 22.9 | 30 | 25 |
| Aluminum Chlorhydrate (Locron L) | | 20 | | 10 | | | |
| Chitosan (Hydagen ® DCMF) | 0.05 | | | | | | |
| Glycolic Acid | 0.02 | | | | | | |
| Glycerin | | | 5 | 5 | | | |
| Propylene Carbonate (Fluka) | | | | | | | 0.5 |
| Quaternium-18 Hectorite (Bentone 18) | | | | | | | 1 |
| Polyquaternium-37 (Ultragel 37) | | 5 | | | | | |
| Talcum (Merck) | | | | | | 5 | 5 |
| MgSO₄ × 7H₂O | | | 1 | | | | |
| Water, Perfume, Preservatives | q.s. | q.s. | q.s. | q.s. | q.s. | q.s. | q.s. |

1/2—Antiperspirant/Deo Cream, 3—Antiperspirant Cream (W/O), 4—Antiperspirant/Deo Spray, 5—Antiperspirant stick with vitamin E, 6—Antiperspirant Cream, 7—Antiperspirant Cream 'Soft Solid'

TABLE 13

| Ingredient (INCI) | 1 | 2 | 3 | 5 | 6 | 7 | 8 |
|---|---|---|---|---|---|---|---|
| Hair-care Conditioner | | | | | | | |
| Structure ® XL (*) (Hydroxypropyl Starch Phosphate) | 5.0 | 5.0 | 5.0 | 4.0 | | | |
| Emulgade ® Sucro (Sucrose Polystearate, Hydrogenated Polyisobutene) | | | | | 1.0 | 1.0 | 1.0 |
| Dehyquart ® L 80 (Dicocoylethyl Hydroxyethylmonium Methosulfate, Propylene Glycol) | 2.6 | 1.3 | 2.0 | | | 0.5 | 0.5 |
| Dehyquart ® F 75 (Distearoylethyl Hydroxyethylmonium Methosulfate, Cetearyl Alcohol) | | | 2.0 | | | | |
| Dehyquart ® C 304 (Aqua, Cocamidopropyl-trimonium Methosulfate, Propylene Glycol) | | | | | 3.7 | 4.0 | 4.0 |

TABLE 13-continued

Hair-care Conditioner

| Ingredient (INCI) | 1 | 2 | 3 | 5 | 6 | 7 | 8 |
|---|---|---|---|---|---|---|---|
| Propylheptyl-methylether or di(2-propylheptyl) ether | 1.0 | 3.0 | 1.0 | 0.5 | 2.0 | 1.5 | 1.5 |
| Dehyquart ® A CA (Cetrimonium Chloride) | | | | | 4.0 | | |
| DC 200 (***) (Dimethicone) | | | | 0.5 | | | |
| Lanette ® O (Cetearyl Alcohol) | | | 1.0 | | 4.0 | | |
| Lamesoft ® TM Benz (Glycol Distearate, Coco Glucoside, Glyceryl Oleate, Glyceryl Stearate) | 4.0 | | | 1.0 | | | |
| Gluadin ® WLM (Hydrolyzed Wheat Protein) | 1.0 | 1.0 | | 1.0 | | | 0.3 |
| Glycerin | | | 0.5 | | | | |
| Gluadin ® Soy (Hydrolyzed Wheat Protein) | | 0.5 | | | | | |
| Cacao Butter (**) Theobroma Cacao (Cocoa) Seed Butter | | | 0.5 | | | | |
| Herbalia ® Balm Mint (Melissa Officinalis, Maltodextrin, Silica) | | 0.01 | | | | | 0.02 |
| Ultragel ™ 300 (Polyquarternium-37) | | | | | | 0.2 | 0.2 |
| Perfume, preservative | q.s. | q.s. | q.s. | q.s. | q.s. | q.s. | q.s. |
| Water | | | | to 100 | | | |

(*) National Starch,
(**) Nederland,
(***) Dow Corning;
pH adjusted to 3.5-5.0

TABLE 14

Hair-care Conditioners

| Ingredient (INCI) | 9 | 10 | 11 | 12 |
|---|---|---|---|---|
| Dehyquart ® L 80 (Dicocoylethyl Hydroxyethylmonium Methosulfate, Propylene Glycol) | 1.3 | 1.3 | | 1.0 |
| Dehyquart ® F 75 (Distearoylethyl Hydroxyethylmonium Methosulfate, Cetearyl Alcohol) | 1.3 | 1.3 | 1.3 | 1.5 |
| Lanette ® O (Cetearyl Alcohol) | 5.0 | 5.0 | 4.0 | 4.5 |
| Propylheptyl-methylether or di(2-propylheptyl) ether | 1.0 | 1.0 | 1.0 | 0.5 |
| Cetiol ® SB 45 Butyrospermum Parkii (Shea Butter) | 4.0 | 4.0 | 2.0 | 4.5 |
| Gluadin ® Almond (Hydrolyzed Sweet Almond Protein) | | | 0.1 | 0.5 |
| ASCO BTAC (Behentrimonium Chloride) | | | 1.3 | |
| DC 949 (****) Amodimethicone, Trideceth-12, Cetrimonium Chloride | | 1.0 | | |
| Cegesoft ® PFO (Passiflora Incarnata Seed Oil) | | | | 2.0 |
| Aloveria ® (Aloe Barbadensis) | 0.1 | | | |
| Sphingoceryl ® Veg: Octyldodecanol, Hydrogenated Coco Glycerides, Helianthus Annuus (Sunflower) Seed Extract | 1.0 | | | |
| Copherol ® 1250 (Tocopheryl Acetate) | 0.2 | | | |
| Ultragel ™ 300 (Polyquarternium-37) | | 0.1 | | 0.2 |
| Perfume, preservative | q.s. | q.s. | q.s. | q.s. |
| Water | | | to 100 | |

(****) Dow Corning; pH adjusted to 3.5-5.0

TABLE 15

Hair-care Conditioner

| | 13 | 14 | 15 | 16 |
|---|---|---|---|---|
| Propylheptyl-methylether or di(2-propylheptyl) ether | 10 | 10.6 | 43.6 | 30 |
| Myritol ® 318 (Caprylic Capric Triglyceride) | | | 43.6 | 20 |
| Cetiol ® ISL (Isostearyl Lactate) | | | | 40 |
| DC 1501 (*) (Cyclomethicone, Dimethiconol) | 69.5 | | | |
| Emery ® 3004 (Hydrogenated Polydecene) | | 67.8 | | |
| DC 345 (*) Cyclomethicone | 20 | | | |
| Versagel MC 750 (**) Isohexadecene, Ethylene/Propylene/Styrene Copolymer, Butylene/Ethylene/Styrene Copolymer | | 21.3 | | |
| DC 556 (*) Phenyl Trimethicone | 0.5 | | | |
| Wacker HDK H 20 (***): Phenyl Trimethicone | | | 12.5 | 10 |
| Ultragel ™ 300 (Polyquarternium-37) | 0.2 | | | 0.2 |
| Perfume | q.s. | q.s. | q.s. | q.s. |

(*) Dow Corning,
(**) Penreco,
(***) Wacker

TABLE 16

Hair-care Conditioner

| Ingredients (INCI) | 17 | 18 | 19 | 20 | 21 |
|---|---|---|---|---|---|
| Cetearyl Alcohol (Lanette ® O) | 5.0 | 4.5 | | | |
| Glyceryl Stearate (Cutina ® MD) | 4.0 | | | 14.5 | |
| Cetearyl Alcohol (Lanette ® O) | | | | 7.0 | |
| Hydrogenated Castor Oil (Cutina ® HR) | | | | 2.5 | |
| Cetyl Palmitate (Cutina ® CP) | | 0.3 | | 7.0 | |
| Paraffin Oil | | | | 23.5 | |
| Vaseline | | | | 32.5 | |
| Wacker Silicon Oil AK 350 | | | | 0.5 | |
| Propylheptyl-methylether or di(2-propylheptyl) ether | 3.0 | 0.2 | 1.5 | 2.0 | 5.0 |

TABLE 16-continued

Hair-care Conditioner

| Ingredients (INCI) | 17 | 18 | 19 | 20 | 21 |
|---|---|---|---|---|---|
| Oleyl Erucate (Cetiol ® J 600) | 2.0 | | | | |
| PEG-7 Glyceryl Cocoate (Cetiol ® HE) | | | | | 20.0 |
| Dimethicone (Dow Corning 200) | | 0.2 | | | |
| Ceteareth-12 (Eumulgin ® B1) | 1.0 | | | | |
| Ceteareth-20 (Eumulgin ® B2) | | 0.4 | | | |
| Ceteareth-30 (Eumulgin ® B3) | | | | | 14.0 |
| Cetoleth-20 (Eumulgin ® O20) | | | | 5.0 | |
| Glycerin, Glyceryl Polyacrylate (Hispagel ® 200) | | | 36.7 | | |
| Lauryl Glucoside (Plantacare ® 1200 UP) | | | | 5.0 | |
| Laureth-7 Citrate (Plantapon ® LC 7) | | 0.7 | 1.0 | | |
| *Glycine Soya* (Soybean) Sterols (Generol ® 122 N) | 0.5 | | | | |
| Hydrogenated Dimer Dilinoleyl/Dimethylcarbonate Copolymer (Cosmedia ® DC) | 1.0 | | | | |
| Glycerin | 3.0 | | | | |
| Cocamide MEA (Comperlan ® 100) | | | | 2.5 | |
| Cetrimonium Chloride (Dehyquart ® A) | 3.0 | 4.0 | | | |
| Hydrolyzed Keratin (Nutrilan ® Keratin W) | 2.0 | | | | |
| PVP/VA (Luviskol ® VA 64) | | | 4.5 | | |
| PEG-90M (Polyox ® WSR-301) | | | 0.25 | | |
| Hydroxypropyl Methylcellulose (Methocel ® E4M Premium EP) | | | 0.6 | | |
| Dicocoylethyl Hydroxyethylmonium Methosulfate, Propylene Glycol (Dehyquart ® L 80) | | | 0.6 | | |
| Triethanolamine | | | 1.0 | | |
| CaCl$_2$*2H$_2$O | | | 0.1 | | |
| Ethanol | | | 12.0 | | |
| Polyquarternium-37 (Ultragel ™ 300) | 0.2 | | | | |
| Water, Perfume, Preservatives | q.s. | q.s. | q.s. | q.s. | q.s. |

TABLE 17

Rinse-Off Concepts

| Ingredients (INCI) | 1 | 2 | 3 | 4 | 5 | 6 |
|---|---|---|---|---|---|---|
| Sodium Laureth Sulfate (Texapon ® N 70) | 12.9 | | 12.3 | 14.3 | 14.3 | |
| Cocamidopropyl Betaine (Dehyton ® PK 45) | 7.7 | | 5.4 | 5.4 | 5.4 | |
| Laureth-7 Citrate (Plantapon ® LC 7) | 10.0 | 2.5 | | | | 10.0 |
| Guar Hydroxypropyltrimonium Chloride (Cosmedia ® Guar C 261N) | | | 0.25 | 0.2 | | |
| Polyquaternium-7 | | | | 2.5 | | |
| Polyquaternium-10 | | | | | 0.15 | |
| Polyquaternium-44 | | | 1.5 | | 1.5 | |
| Glycol Distearate, Laureth-4, Cocamidopropyl Betaine (Euperlan ® PK 4000) | | | 10.0 | 2.0 | 2.0 | |
| PEG-40 Hydrogenated Castor Oil (Eumulgin ® HRE 40) | | 7.5 | | | | |
| Mineral Oil | | | | | | 55.0 |
| (Propylheptyl Caprylate) Cetiol ® Sensoft | | | | | | 29.0 |
| Propylheptyl-methylether or di(2-propylheptyl) ether | 1.0 | 2.0 | 1.0 | 0.5 | 0.5 | 0.5 |
| Lauryl Alcohol | | | 0.5 | 0.5 | 0.5 | |
| Sodium Chloride | | | adjust viscosity | | | |
| Ethanol | | 25.0 | | | | |
| Water, Perfume, Preservatives | q.s. | q.s. | q.s. | q.s. | q.s. | q.s. |
| pH (adjusted with NaOH or citric acid) | 5.5 | 6.0 | 5.5 | 5.7 | 5.4 | 5.5 |

TABLE 18

Rinse-Off Concepts

| Ingredients (INCI) | 7 | 8 | 9 | 10 | 11 | 12 |
|---|---|---|---|---|---|---|
| MIPA-Laureth Sulfate, Laureth-4, Propylene Glycol (Texapon ® W 90) | 40.7 | 28.3 | 28.3 | 28.3 | 28.3 | |
| Sodium Laureth Sulfate (Texapon ® N 70) | | | | | | 10.9 |
| Coco-Glucoside (Plantacare ® 818 UP) | | | | | | 6.9 |
| Laureth-7 Citrate (Plantapon ® LC 7) | 5.0 | 28.3 | 28.3 | 28.3 | 28.3 | |
| Laureth-2 (Mergital ® LM2 DEO) | 10.0 | | | | | |
| PEG-7 Glyceryl Cocoate (Cetiol ® HE) | 1.1 | | | | | |
| Soya Oil | | | 20.7 | | | |
| Almond Oil | | | | | | 0.5 |
| Paraffinum Liquidum | | | | | 7.0 | 23.0 |
| Cyclomethicone (Dow Corning ® 245) | | | | | | |
| Dimethicone Copolyol (Dow Corning ® 193) | | | | 1.0 | | |
| Olus (Cegesoft ® PS6) | 22.0 | | | | | 10.0 |
| Propylheptyl-methylether or di(2-propylheptyl) ether | 20.0 | 41.4 | 20.7 | 40.4 | 34.4 | 15.0 |
| Acrylates Copolymer (Carbopol ® Aqua) | | | | | | 4.0 |

TABLE 18-continued

| Ingredients (INCI) | Rinse-Off Concepts | | | | | |
|---|---|---|---|---|---|---|
| | 7 | 8 | 9 | 10 | 11 | 12 |
| Acrylates/C10-30 Alkyl Acrylate Crosspolymer (Pemulen ® TR-1) | | | | | | 0.5 |
| AMP ® 95 | 1.2 | | | | | |
| Poloxamer ® 101 | | 2.0 | 2.0 | 2.0 | 2.0 | |
| Water | | | q.s. | | | |

APPENDIX

Ingredients

AMP-95, INCI: Aminomethyl Propanol, Dow Chemical Co; Abil® EM 90; INCI: Cetyl Dimethicone Copolyol; Tego Cosmetics (Goldschmidt); Allianz® OPT; INCI: Acrylates/C12-22 Alkyl Methacrylate Copolymer; Rohm and Haas; Amphisol® K; INCI: Potassium Cetyl Phosphate; Hoffmann La Roche; Admul® WOL 1403, INCI: Polyricinoleate of polyglycerol, Quest; Antaron® V 220; INCI: PVP/Eicosene Copolymer; GAF General Aniline Firm Corp. (IPS-Global); Antaron® V 216; INCI: PVP/Hexadecene Copolymer: GAF General Aniline Firm Corp. (IPS-Global); Arlacel® 83; INCI: Sorbitan Sesquioleate, Uniqema (ICI Surfacants); Arlacel® P 135, INCI: PEG-30 Dipolyhydroxystearate, Uniqema (ICI Surfacants); Bentone® 38, INCI: Quaternium-18 Hectorite, Rheox (Elementis Specialties); Carbopol® 980, INCI: Carbomer, Goodrich; Carbopol® 2984, INCI: Carbomer, Noveon, Inc.; Carbopol® ETD 2001, INCI: Carbomer, Noveon, Inc.; Carbopol® Ultrez 10, INCI: Carbomer; Noveon, Inc.; Cegesoft® C 17, Myristyl Lactate, Cognis GmbH; Cegesoft® PFO, INCI: Passiflora Incarnata (EU); Cognis GmbH; Cegesoft® PS 6, INCI: Olus, Cognis GmbH, Cegesoft® SH, INCI: Shorea Stenoptera Seed Butter Cognis GmbH; Ceraphyl® 45, INCI: Diethylhexyl Malate, International Specialty Products; Cetiol® 868, INCI: Ethylhexyl Stearate, Manufacturer: Cognis GmbH; Cetiol® A, INCI: Hexyl Laurate, Cognis GmbH; Cetiol® B, INCI: Dibutyl Adipate, Cognis GmbH; Cetiol® CC, INCI: Dicaprylyl Carbonate; Cognis GmbH; Cetiol® J 600, INCI: Oleyl Erucate, Cognis GmbH; Cetiol® LC, INCI: Coco-Caprylate/Caprate, Cognis GmbH; Cetiol® MM, INCI: Myristyl Myristate, Cognis GmbH; Cetiol® OE, INCI: Dicaprylyl Ether, Cognis GmbH, Cetiol® PGL, INCI: Hexyldecanol, Hexyldecyl Laurate, Cognis GmbH; Cetiol® S, INCI: Diethylhexylcyclohexane, Cognis GmbH; Cetiol® SB 45, INCI: Shea Butter Butyrospermum Parkii (Linne), Cognis GmbH; Cetiol® SN, INCI: Cetearyl Isononanoate, Cognis GmbH, Copherol® F 1300 C, INCI: Tocopherol, Cognis GmbH; Copherol 1250 C, INCI: Tocopheryl Acetate, Cognis GmbH; Cosmedia® DC, INCI: Hydrogenated Dimer Dilinoleyl/Dimethylcarbonate Copolymer; Cognis GmbH; Cosmedia® SP, INCI: Sodium Polyacrylate; Cognis GmbH; Cutina® E 24, INCI: PEG-20 Glyceryl Stearate; Cognis GmbH; Cutina® HR, INCI: Hydrogenated Castor Oil, Cognis GmbH; Cutina® MD, INCI: Glyceryl Stearate, Cognis GmbH; Cutina® PES, INCI: Pentaerythrityl Distearate, Cognis GmbH; Cutina® FS-45, INCI: Palmitic Acid, Stearic Acid, Cognis GmbH; Cutina® GMS-SE, INCI Glyceryl Stearate SE, Cognis GmbH; Cutina® LM conc, INCI: Polyglyceryl-2 Dipolyhydroxystearate, Octyldodecanol, Copernicia Cerifera (Carnauba) Wax, Euphorbia Cerifera (Candelilla) Wax, Beeswax, Cetearyl Glucoside, Cetearyl Alcohol, Cognis GmbH; Dehymuls® FCE, INCI: Dicocoyl Pentaerythrityl Distearyl Citrate, Cognis GmbH; Dehymuls® HRE 7, INCI: PEG-7 Hydrogenated Castor Oil, Cognis GmbH; Dehymuls® PGPH, INCI: Polyglyceryl-2 Dipolyhydroxystearate, Cognis GmbH; Crodesta® F-50, INCI Sucrosedistearate, Croda; Dehymuls® LE, INCI: PEG-30 Dipolyhydroxystearate, Cognis GmbH; Dow Corning® 244 Fluid, INCI: Cyclomethicone, Dow Corning; Dow Corning® 246 Fluid, Cyclopentasiloxane, Dow Corning; Dow Corning® 2502, INCI: Cetyl Dimethicone, Dow Corning; Dow Corning DC® 245 INCI: Cyclopentasiloxane, Dow Corning, Dehyquart® C 4046, INCI: Cetearyl Alcohol, Dipalmitoylethyl Hydroxyethylmonium Methosulfate, Ceteareth-20, Cognis GmbH; Dry® Flo Plus, INCI: Aluminum Starch Octenylsuccinate, National Starch; Dry® Flo PC, INCI: Aluminum Starch Octenylsuccinate, Akzo Nobel; Elfacos® ST 37, INCI: PEG-22 Dodecyl Glycol Copolymer, Akzo-Nobel; Elfacos® ST 9, INCI: PEG-45 Dodecyl Glycol Copolymer, Akzo-Nobel; Emery® 1780, INCI: Lanolin Alcohol, Cognis Corp.; Emulgade® CM, INCI: Cetearyl Isononanoate and Ceteareth-20 and Cetearyl Alcohol and Glyceryl Stearate and Glycerin and Ceteareth-12 and Cetyl Palmitate, Cognis GmbH; Emulgade® PL 68/50, INCI: Cetearyl Glucoside, Cetearyl Alcohol, Cognis GmbH; Emulgade® SE-PF, INCI: Glyceryl Stearate (and) Ceteareth-20 (and) Ceteareth-12 (and) Cetearyl Alcohol (and) Cetyl Palmitate; Cognis GmbH, Emulgade® SUCRO, INCI: Sucrose Polystearate (and) Hydrogenated Polyisobutene, Cognis GmbH; Eumulgin® B1, INCI: Ceteareth-12, Cognis GmbH, Eumulgin® B 2, INCI: Ceteareth-20, Cognis GmbH; Eumulgin® HRE 40, INCI: PEG-40 Hydrogenated Castor Oil, Cognis GmbH; Eumulgin® Prisma INCI: Disodium Cetearyl Sulfosuccinate; Eumulgin® SG, INCI: Sodium Stearoyl Glutamate, Cognis GmbH; Eumulgin® VL 75, INCI: Lauryl Glucoside (and) Polyglyceryl-2 Dipolyhydroxystearate (and) Glycerin; Cognis GmbH; Eusolex® OCR, INCI: Octocrylene, Merck; Eusolex® T 2000, INCI: Titanium Dioxide, Alumina, Simethicone, Merck; Eusolex® AQUA, INCI: Water and Titanium Dioxide and Alumina and Sodium Metaphosphate and Phenoxyethanol and Sodium Methylparaben, Merck; Eutanol® G, INCI: Octyldodecanol, Cognis GmbH; Eutanol® G 16, INCI: Hexyldecanol, Cognis GmbH; Eutanol® G 16 S, INCI: Hexyldecyl Stearate, Cognis GmbH; Finsolv® TN, INCI: C 12/15 Alkyl Benzoate, Findex (Nordmann/Rassmann); Fitoderm®, INCI Squalane, Cognis GmbH; Generol® R, INCI: Brassica Campestris (Rapeseed) Sterols, Cognis GmbH; Glucate® DO, INCI: Methyl Glucose Dioleate, NRC Nordmann/Rassmann; Hispagel® 200, INCI: Glycerin, Glyceryl Polyacrylate, Cognis GmbH; Hostaphat® KL 340 N, INCI: Trilaureth-4 Phosphate, Clariant; Hydagen® C.A.T., INCI Triethyl Citrate, Cognis GmbH; Hydagen® DCMF, INCI: Chitosan, Cognis GmbH; Insect Repellent® 3535, INCI: Ethyl Butylacetylaminopropionate, EMD Chemicals Inc; Isolan® PDI, INCI: Diisostearoyl Polyglyceryl-3 Diisostearate, Goldschmidt AG; Isolan® GPS, INCI: Polyglyceryl-4 Diisostearate/Polyhydroxystearate/Sebacate, Evonik Goldschmidt; Isolan® GI 34, INCI: Polyglyceryl-4 Isostearate, Evonik Goldschmidt; Irwinol® LS 9319, INCI: Octyldecanol, Irvingia Gabonensis Kernel Butter, Hydrogenated Coco-Glycerides, Keltrol®, INCI: Xanthan Gum, CP Kelco; Lameform® TGI, INCI: Polyglyceryl-3 Diisostearate, Cognis GmbH; Lanette® 14, INCI: Myristyl Alcohol, Cognis GmbH; Lanette® 18, INCI: Stearyl Alcohol, Cognis GmbH; Lanette® 22, INCI: Behenyl Alcohol, Cognis GmbH; Lanette® E, INCI: Sodium Cetearyl Sulfate, Cognis GmbH; Lanette® O, INCI: Cetearyl Alcohol, Cognis GmbH; Locron® L, INCI: Aluminum Chlorhydrate, Clariant; Lucentite® SAN, INCI: Quaternium-18 Hectorite, Co-Op Chemical Co., Ltd.; Microna® Matte White (INCI: Titanium Dioxide, Zinc Oxide); Microna® Matte Black (INCI: Iron Oxide; Mica); Microna® Matte Yellow (INCI: Iron Oxide; Mica); Microna® Matte Red (INCI: Iron Oxide; Mica), Cosmetic white C47056 (INCI: Titanium Dioxide, Mica); FDC Yellow 6 AI Lake C705270 (INCI: Color Index 15985); DC Red 7 Ca Lake C 19003 (INCI: Color Index 15850); Irodin 100 Silverpearl, (INCI: Mica, Titanium dioxide); Colophane Claire type Y (INCI: Colophonium); Monomuls® 90-O 18, INCI: Glyceryl Oleate, Cognis GmbH; Monomuls® 90 L 12, INCI: Glyceryl Laurate, Cognis GmbH; Myrj® 51, INCI: PEG-30-Stearate, Uniqema; Myritol® 312, INCI: Caprylic/Capric Triglyceride, Cognis GmbH; Myritol® 331, INCI: Cocoglycerides, Cognis GmbH; Myritol® PC, INCI: Propylene Glycol Dicaprylate/Dicaprate, Cognis GmbH; Neo Heliopan® 303, INCI: Octocrylene, Symrise; Neo Heliopan® AP, INCI: Disodium Phenyl Dibenzimidazole Tetrasulfonate, Symrise; Neo Heliopa® AV, INCI: Ethylhexyl Methoxycinnamate, Symrise; Neo Heliopan® BB, INCI: Benzophenone-3, Symrise; Neo Heliopan® E 1000, INCI: Isoamyl-p-Methoxycinnamate, Symrise; Neo Heliopan® Hydro, INCI: Phenylbenzimidazole Sulfonic Acid, Symrise; Neo Heliopan® MBC, INCI: 4-Methylbenzylidene Camphor, Symrise; Neo Heliopan® OS, INCI: Ethylhexyl Salicylate, Symrise; Novata® AB, INCI: Cocoglycerides, Cognis GmbH; Parsol® 1789, INCI: Butyl Methoxydibenzoylmethane, Hoffmann-La Roche (Givaudan); Pemulen® TR-2 Polymer, INCI: Acrylates/C10-30 Alkylacrylate Crosspolymer, Noveon, Inc.; Photonyl® LS, INCI: Arginine, Disodium Adenosine Triphosphate, Mannitol, Pyridoxine HCL, Phenylalanine, Tyrosine, Laboratoires Serobiologiques (Cognis); Prisorine® 3505, INCI: Isostearic Acid; Uniqema; Prisorine® 3758, INCI: Hydrogenated Polyisobutene, Uniqema; Rezal 36G, INCI: Aluminum Zirconium Tetrachlorohydrex GLY, Reheis, Inc; Rheocare® C Plus, INCI Carbomer, Cognis GmbH; Ronasphere® LDP, INCI: Silica, Titanium Dioxide, Iron Oxides; Squatol® S, INCI: Hydrogenated Polyisobutene, BASF Corp.; Poloxamer® 101, INCI: Poloxamer, BASF SE; SFE® 839, INCI: Cyclopentasiloxane and Dimethicone/Vinyl Dimethicone Crosspolymer, GE Silicones; Silicone oil Wacker AK® 350, INCI: Dimethicone, Wacker; Tego® Care 450, INCI: Polyglyceryl-3 Methylglucose Distearate, Goldschmidt; Tego® Care CG 90, INCI: Cetearyl Glucoside, Goldschmidt; Tegosoft® DEC, INCI: Diethylhexyl Carbonate, Goldschmidt; Tinosorb® S, INCI: Bis-Ethylhexyloxyphenol Methoxyphenyl Triazine; Ciba Specialty Chemicals Corporation; Tinosorb® M, INCI: Methylene Bis-Benzotriazolyl Tetramethylbutylphenol, Ciba Specialty Chemicals Corporation; Tween® 60, INCI: Polysorbate 60, Uniqema (ICI Surfactants), Uvasorb® HEB, INCI: Diethylhexyl Butamido Triazone, 3V Inc.; Unirep® U-18, INCI: Dimethyl Phthalate and Diethyl Toluamide and Ethyl Hexanediol, Induchem AG; Uvinul® T 150, INCI: Ethylhexyl Triazone, BASF; Uvinul® A plus, INCI: Diethylamino Hydroxybenzoyl Hexyl Benzoate, BASF; Veegum® Ultra, INCI: Magnesium Aluminum Silicate, R. T. Vanderbilt Company, Inc; Veegum® Plus, INCI: Magnesium Aluminum Silicate and Cellulose Gum, R. T. Vanderbilt Company, Inc; Z-Cote® HP 1, INCI: Zinc Oxide and Triethoxy-caprylylsilane, BASF, Zinc Oxide NDM, INCI: Zinc Oxide, Symrise.

The invention claimed is:

1. A compound of general formula (I)

$R_1$—O—$R_2$, wherein $R_1$ and $R_2$ are selected from the group consisting of 2-propylheptyl, 3-methyl-2-propyl-hexyl, 4-methyl-2-propyl-hexyl and 5-methyl-2-propyl-hexyl.

2. The compound according to claim 1, wherein $R_1$ represents a 2-propylheptyl residue.

3. The compound according to claim 1, wherein $R_1$ and $R_2$ represent a 2-propylheptyl residue.

4. A method of producing a cosmetic and/or pharmaceutical preparation, the method comprising incorporating one or more compounds according to claim 1 in a cosmetic and/or pharmaceutical preparation.

5. The method according to claim 4, wherein the one or more compounds are incorporated as oily substances.

6. A cosmetic and/or pharmaceutical preparation comprising 0.1 to 95 wt % of one or more compounds according to claim 1 in a cosmetically and/or pharmaceutically suitable vehicle and an optional cosmetic auxiliary ingredient.

7. The compound according to claim 1, wherein $R_1$ and $R_2$ are identical.

8. The cosmetic and/or pharmaceutical composition according to claim 6, wherein $R_1$ and $R_2$ are identical.

* * * * *